US006671050B2

(12) United States Patent
Sugiyama et al.

(10) Patent No.: US 6,671,050 B2
(45) Date of Patent: Dec. 30, 2003

(54) COLOR MEASURING METHOD AND DEVICE FOR PRINTED MATTER

(75) Inventors: Tohru Sugiyama, Tokyo (JP); Yoshiaki Kudo, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 30 days.

(21) Appl. No.: 10/016,135

(22) Filed: Nov. 1, 2001

(65) Prior Publication Data

US 2002/0135768 A1 Sep. 26, 2002

(30) Foreign Application Priority Data

Nov. 6, 2000 (JP) ........................................ 2000-338134

(51) Int. Cl.$^7$ ............................................. G01N 21/25
(52) U.S. Cl. ......................................... 356/405; 356/73
(58) Field of Search .................................... 356/405, 73

(56) References Cited

U.S. PATENT DOCUMENTS

| 4,699,510 A | * | 10/1987 | Alguard | ........................ | 356/73 |
| 5,384,641 A | * | 1/1995 | Imura | ........................ | 356/446 |
| 6,020,959 A | * | 2/2000 | Imura | ........................ | 356/319 |

FOREIGN PATENT DOCUMENTS

| JP | 11-27546 | * | 1/1999 | ............ | H04N/1/60 |

OTHER PUBLICATIONS

Kudo, Yoshiaki et al. Pre Print, The 105$^{th}$ Fall Conference, Japanese Society of Printing Science and Technology, (2000).

Kudo, Yoshiaki et al. Pre Print, The 106$^{th}$ Spring Conference, Japanese Society of Printing Science and Technology (2001).

* cited by examiner

Primary Examiner—F. L. Evans
Assistant Examiner—Kara Geisel
(74) Attorney, Agent, or Firm—Ladas & Parry

(57) ABSTRACT

The indication of correct color evaluation standards of a printed matter including a paper containing a fluorescent whitening agent, is enabled even in the case where the printed matter is observed under a light source that differs from the light source used for color measurement. A spectral reflectance $Pt(\lambda)$ of the paper under a light source T and a spectral reflectance $Pu(\lambda)$ of the paper under a light source U are measured in advance and a differential component, due to the fluorescent whitening agent, is determined as $Fp(\lambda)=Pu(\lambda)-Pt(\lambda)$. For a printed matter of dot percent S, a spectral reflectance $Rt(\lambda, S)$ under light source T is measured, and the measured values are subject to a correction process of adding an effective component within the differential component $Fp(\lambda)$ that is in accordance to dot percent S to determine an estimated spectral reflectance $Rtu(\lambda, S)$ under light source U. Estimation in likewise manner can also be performed for XYZ tristimulus values.

30 Claims, 9 Drawing Sheets

R(λ): SPECTRAL TRANSMITTANCE OF INK-ADHERED PART

P(λ): SPECTRAL TRANSMITTANCE OF NON-INK-ADHERED PART

COLOR MEASURING METHOD AND DEVICE FOR PRINTED MATTER

BACKGROUND OF THE INVENTION

This invention concerns a color measuring method and device for printed matter, and in particular, concerns a color measuring method and device by which the differences in measurement results according to light source can be corrected. In many cases in the printing industry, the color of a specific part of each individual printed matter must be ascertained as an objective, numerical value. Various color measuring methods for printed matter have thus been known conventionally and various color measuring devices are actually being used.

In general, the color of an object is determined by the spectral reflectance of the object, the spectral intensity distribution of the light that illuminates the object, and the spectral sensitivity distribution of the visual system of the human being who is observing the object. A spectral reflectance that is measured for an object will thus be an important set of objective data that indicate the color of the object. However, the color of an object is also strongly affected by the spectral intensity distribution of the light that illuminates the object, in other words, by the spectral intensity distribution of the light source. Thus, for example, under a light source that contains a high amount of a red color component, the color of the object will be observed to be reddish. Therefore, the spectral intensity distribution of the light source is normally taken into consideration in measuring a spectral reflectance of an object.

To be more specific, the measurement of a spectral reflectance of a sample that is to be measured is carried out for example by the following method. First, a "perfect reflecting diffuser", which is a plate-like object with a smooth surface that does not reflect light specularly and has a spectral reflectance of substantially close to 1.0 across the entire visible range, is prepared. Normally, a plate having barium sulfate or other white powder coated and solidified on the surface is used as the perfect reflecting diffuser. Next, a specific light source is made to illuminates the sample and the spectral intensity distribution of the reflected light that is obtained from the sample at this time is obtained. Next, light is irradiated onto the perfect reflecting diffuser using exactly the same light source and the spectral intensity distribution of the reflected light that is obtained from the perfect reflecting diffuser is obtained. As a device for measuring the spectral intensity distribution, a spectral radiance meter, etc., is generally used. Lastly, by dividing the spectral intensity distribution obtained for the sample by the spectral intensity distribution obtained for the perfect reflecting diffuser, the spectral reflectance of the sample that is not dependent on the light source can be obtained.

When the spectral reflectance of the sample has been obtained in the above manner, elements of the spectral sensitivity distribution of the human visual system are incorporated to provide data that objectively indicate the color that a human being senses in the observation process. The spectral reflectance data are data that indicate the reflectance in the visible wavelength range of 380 nm to 780 nm, and even if data are collected at each 5 nm of wavelength, the data will consist of numerical values indicating 81 values of reflectance and will thus be inconvenient to handle. Thus for color evaluation, a color is generally expressed using the tristimulus values (XYZ) of the XYZ colorimetric system stipulated by the Commission Internationale de l'Eclairage (CIE). The tristimulus values (XYZ) can be determined by a known method (refer for example to ISO/CIE 10527 CIE standard colorimetric observers, 1st Ed., 1991), which uses the spectral reflectance of the sample, the spectral sensitivity distribution of the human visual system, and the spectral intensity distribution of the light source that is used in observation, and are generally referred to as colorimetric values. As the spectral intensity distributions of typical light sources, the spectral intensity distributions, for example, of CIE standard illuminant D65, CIE illuminant D50, etc., which are stipulated in ISO/CIE 10526 CIE standard color illuminants, 1st Ed., 1991 can be used. Also with regard to the spectral sensitivity distribution of the human visual system, the color matching function for the XYZ colorimetric system stipulated in ISO/CIE 10527 CIE standard colorimetric observers, 1st Ed., 1991 can be used.

A general color measuring device for printed matter in the prior art has functions of measuring the color of a specific part of a printed matter based on the above-described principles of measuring color and determining objective data, such as the spectral reflectance, colorimetric values, etc. That is, a general color measuring device has a light source which illuminates light onto a printed matter that is to be measured, a spectral radiance meter which measures the spectral reflectance, and a computational processing unit which carries out various computations, and normally, a perfect reflecting diffuser is provided for carrying out corrections. When an operator performs the necessary computations in accordance to the above-described measurement procedure, the computational processing unit executes the necessary computations based on the collected data and thereby automatically obtains the spectral reflectance, colorimetric values, and other objective data.

With the above-described color measuring method, it should be possible to determine the spectral reflectance and colorimetric values of a sample that do not depend on the light source by carrying out the correction that makes uses of measurement results obtained using a perfect reflecting diffuser. However, in actuality, with a printed matter with which gradation is expressed by an area modulation method, such as offset printing, the measurement results obtained by a conventional color measuring method do not match the colors recognized by a human being in many cases. This is due to a fluorescent whitening (brightening) agent being contained in the printing paper. A fluorescent whitening agent is a colorless compound, which has the property of dyeing fibrous matter and emitting blue to purple fluorescent light corresponding to a wavelength near 420 nm and has the function of whitening the printed paper by emitting light that is complementary to the yellow color of fibers. To be more specific, stilbenzene dyes, etc. are used as fluorescent whitening agents in many printing papers. Though a sheet of paper that is comprised only of normal fibers looks yellowish, a sheet of paper to which a fluorescent whitening agent is added is increased in whiteness due to complementation by a blue to purple color (complementary color of yellow).

However, the intensity of fluorescence is normally strongly dependent on the wavelength of the light source, and a fluorescent whitening agent has the property of fluorescing strongly when illuminated with light of a high amount of ultraviolet components and weakening in fluorescence when illuminated with light of a low amount of ultraviolet components. Paper to which a fluorescent whitening agent is added thus seems bluish when observed under a fluorescent lamp, daytime sunlight, or other light source that contains a high amount of ultraviolet components and seems yellowish when observed under an illumination light source, such as a tungsten lamp. In a printed matter with which gradation is expressed by an area modulation method, such as offset printing, ink is transferred to a paper as a collection of microscopic units of adhesion (halftone dots in the case of offset printing). Gradation is expressed by this units of ink by controlling the area of the ink-adhered part per unit area, in other words the dot percent. The same applies likewise to color printed matter obtained by an inkjet printer. Thus with a halftone printed matter, the bare part of the paper to which ink is not adhered becomes an important element that affects color. For example, a halftone part for which the offset printing dot percent is 50% magenta is observed as a pink-colored part. However, in actuality, a magenta part (ink-adhered part) and a bare part (white paper part) are simply observed in a mixed manner at a fifty-fifty ratio. Thus when the paper contains a fluorescent whitening agent, the actually observed color is greatly affected by the type of light source.

Generally in a color measuring device, a tungsten lamp is used in many cases to make the size of the device itself compact. Thus under the measuring environment of such a color measuring device, the emission of fluorescence from the fluorescent whitening agent contained in the paper will be extremely weak. In other words, the spectral reflectance and colorimetric values obtained by a color measuring device that uses a tungsten lamp as a light source are measurement results obtained under conditions where the fluorescence from the fluorescent whitening agent contained in the paper is weak. However, when the same printed matter is observed under a fluorescent lamp or daytime sunlight, since the fluorescent whitening agent fluoresces strongly, the color will be observed to differ from the color indicated by the measurement results that were obtained under conditions of weak fluorescence. Due to such causes, there is the problem that the measurement results obtained by the prior-art color measuring method does not necessarily match the color recognized by a human occurs in the case of a printed matter that uses paper containing a fluorescent whitening agent.

SUMMARY OF THE INVENTION

This invention has been made to resolve the above-described problem and an object thereof is to provide a color measuring method and device for printed matter by which correct color evaluation standards can be indicated even when a printed matter is observed under a light source that differs from the light source used in the color measuring process.

(1) The first feature of the present invention resides in a color measuring method for determining a spectral reflectance, under a predetermined illumination environment, for a printed matter including a paper containing a fluorescent whitening agent, the method being comprised of:

a first step of measuring a spectral reflectance $Pt(\lambda)$ of the paper under a first illumination environment and a spectral reflectance $Pu(\lambda)$ of the paper under a second illumination environment;

a second step of computing a difference, obtained by subtracting the spectral reflectance $Pt(\lambda)$ from the spectral reflectance $Pu(\lambda)$, as a differential component $Fp(\lambda)$ of the paper due to the fluorescent whitening agent;

a third step of measuring a spectral reflectance $Rt(\lambda)$, under the first illumination environment, for a region to be measured of the printed matter; and a fourth step of performing a correction based on the differential component $Fp(\lambda)$ on the spectral reflectance $Rt(\lambda)$ to compute an estimated spectral reflectance, under the second illumination environment, for the region to be measured.

(2) The second feature of the present invention resides in a color measuring method for printed matter including the first feature, wherein:

in a process of measurement in the first step and the third step, a result of measurement of a spectral reflectance of a perfect reflecting diffuser is used to perform a correction of eliminating influence of spectral intensity distribution of illumination light that is used.

(3) The third feature of the present invention resides in a color measuring method for printed matter including the first or second feature, wherein:

in a process of computation in the fourth step, correction based on the differential component $Fp(\lambda)$ is not performed on an ink-adhered region within the region to be measured.

(4) The fourth feature of the present invention resides in a color measuring method for printed matter including the third feature, wherein:

in the third step, a spectral reflectance $Rt(\lambda, S)$ under the first illumination environment is measured for a region to be measured, a ratio of an area of an ink-adhered region to an entire area in the region to be measured being S;

in the fourth step, a computation using an equation:

$$Rtu(\lambda, S) = Rt(\lambda, S) + Fp(\lambda) \cdot (1-S)^2$$

is performed to determine an estimated spectral reflectance $Rtu(\lambda, S)$, under the second illumination environment, for the region to be measured.

(5) The fifth feature of the present invention resides in a color measuring method for printed matter including the first or second feature, wherein:

in a process of computation in the fourth step, a correction based on the differential component $Fp(\lambda)$ is performed in accordance to an optical transmittance of an ink layer for an ink-adhered region in the region to be measured.

(6) The sixth feature of the present invention resides in a color measuring method for printed matter including the fifth feature, wherein:

in the third step, a spectral reflectance $Rt(\lambda, S)$ under the first illumination environment is measured for a region to be measured, a ratio of an area of an ink-adhered region to an entire area in the region to be measured being S;

in the fourth step, an excitation coefficient CE and a luminescence coefficient CL are defined, the excitation coefficient CE indicating a proportion of "total amount of excitation energy supplied to an ink-adhered part" per unit area with respect to "total amount of excitation energy supplied to a non-ink-adhered part" per unit area in the case where the parts are illuminated under the same conditions from an exterior, the luminescence coefficient CL indicating a proportion of "total amount of luminescence energy emitted from the ink-adhered part and observed" per unit area with respect to "total amount of luminescence energy emitted from the non-ink-adhered part and observed" per unit area in the case where emission of fluorescence from each of the parts occurs under the same conditions inside the paper, the excitation coefficient CE and the luminescence coefficient CL of the region to be measured are measured, and computation using an equation:

$$RRtu(\lambda, S) = Rt(\lambda, S) + Fp(\lambda) \cdot (1 - S(1-CE)) \cdot (1 - S(1-CL))$$

is performed to determine an estimated spectral reflectance $RRtu(\lambda, S)$, under the second illumination environment, for the region to be measured.

(7) The seventh feature of the present invention resides in a color measuring method for printed matter including the fifth feature, wherein:

in the third step, a spectral reflectance $Rt(\lambda, S_1, S_2, S_{12})$ under the first illumination environment is measured for a region to be measured, ratios of areas of a first region, a second region, a third region and a fourth region with respect to an entire area in the region to be measured being $S_1$, $S_2$, $S_{12}$, $S_p$, respectively, only a first ink being adhered in the first region, only a second ink being adhered in the second region, both the first ink and the second ink being adhered in the third region, and neither ink being adhered in the fourth region;

in the fourth step, an excitation coefficient CE and a luminescence coefficient CL are defined, the excitation coefficient CE indicating a proportion of "total amount of excitation energy supplied to an ink-adhered part" per unit area with respect to "total amount of excitation energy supplied to a non-ink-adhered part" per unit area in the case where the parts are illuminated under the same conditions from an exterior, the luminescence coefficient CL indicating a proportion of "total amount of luminescence energy emitted from the ink-adhered part and observed" per unit area with respect to "total amount of luminescence energy emitted from the non-ink-adhered part and observed" per unit area in the case where emission of fluorescence from each of the parts occurs under the same conditions inside the paper, excitation coefficients $CE_1$, $CE_2$, and $CE_{12}$ and luminescence coefficients $CL_1$, $CL_2$, and $CL_{12}$ of the first region, the second region, and the third region, respectively, are measured, and computation using an equation:

$$RRtu(\lambda, S_1, S_2, S_{12}) = Rt(\lambda, S_1, S_2, S_{12}) + Fp(\lambda) \cdot (S_p + S_1 \cdot CE_1 + S_2 \cdot CE_2 + S_{12} \cdot CE_{12}) \cdot (S_p + S_1 \cdot CL_1 + S_2 \cdot CL_2 + S_{12} \cdot CL_{12})$$

is performed to determine an estimated spectral reflectance $RRtu(\lambda, S_1, S_2, S_{12})$, under the second illumination environment, for the region to be measured.

(8) The eighth feature of the present invention resides in a color measuring method for printed matter including the fifth feature, wherein:

in the third step, a spectral reflectance under the first illumination environment is measured for a region to be measured, on which printing using a plurality of inks is performed and a total of n kinds of ink-adhered regions are formed by mixing of a first type of region in which only an ink of a single color is adhered and a second type of region in which a plurality of inks are adhered in an overlapping manner, a ratio of an area of an i-th region with respect to an entire area in the region to be measured being Si;

in the fourth step, an excitation coefficient CE and a luminescence coefficient CL are defined, the excitation coefficient CE indicating a proportion of "total amount of excitation energy supplied to an ink-adhered part" per unit area with respect to "total amount of excitation energy supplied to a non-ink-adhered part" per unit area in the case where the parts are illuminated under the same conditions from an exterior, the luminescence coefficient CL indicating a proportion of "total amount of luminescence energy emitted from the ink-adhered part and observed" per unit area with respect to "total amount of luminescence energy emitted from the non-ink-adhered part and observed" per unit area in the case where emission of fluorescence from each of the parts occurs under the same conditions inside the paper, and the excitation coefficient CE and the luminescence coefficient CL of each of the n kinds of ink-adhered regions are measured; and in a process of computation in the fourth step, a correction based on the differential component $Fp(\lambda)$ is performed on the n kinds of ink-adhered regions in the region to be measured in accordance to the excitation coefficients CE and the luminescence coefficients CL determined for the respective n kinds of ink-adhered regions.

(9) The ninth feature of the present invention resides in a color measuring method for printed matter including the sixth, seventh or eighth feature, wherein:

a spectral transmittance $R(\lambda)$ of the ink-adhered part, a spectral transmittance $P(\lambda)$ of the non-ink-adhered part, an excitation spectrum $PE(\lambda)$ of the paper, and a luminescence spectrum $PL(\lambda)$ of the paper are measured; and the excitation coefficient CE and the luminescence coefficient CL of the ink-adhered part are determined using the following equations:

$$CE = \int R(\lambda) \cdot PE(\lambda) d\lambda / \int P(\lambda) \cdot PE(\lambda) d\lambda$$

$$CL = \int R(\lambda) \cdot PL(\lambda) d\lambda / \int P(\lambda) \cdot PL(\lambda) d\lambda.$$

(10) The tenth feature of the present invention resides in a color measuring method for determining XYZ tristimulus values, under a predetermined illumination environment, for a printed matter including a paper containing a fluorescent whitening agent, the method being comprised of:

a first step of measuring XYZ tristimulus values Pt(X), Pt(Y), and Pt(Z) of the paper under a first illumination environment and XYZ tristimulus values Pu(X), Pu(Y), and Pu(Z) of the paper under a second illumination environment;

a second step of computing differences, obtained by subtracting the XYZ tristimulus values Pt(X), Pt(Y), and Pt(Z) from the XYZ tristimulus values Pu(X), Pu(Y), and Pu(Z), respectively, as differential components Fp(X), Fp(Y), and Fp(Z) of the paper due to the fluorescent whitening agent;

a third step of measuring XYZ tristimulus values Rt(X), Rt(Y), and Rt(Z), under the first illumination environment, for a region to be measured of the printed matter; and a fourth step of performing corrections based on the differential components Fp(X), Fp(Y), and Fp(Z) on the XYZ tristimulus values Rt(X), Rt(Y), and Rt(Z), respectively, to compute estimated XYZ tristimulus values, under the second illumination environment, for the region to be measured.

(11) The eleventh feature of the present invention resides in a color measuring method for printed matter including the tenth feature, wherein:
in a process of measurement in the first step and the third step, XYZ tristimulus values are determined by computation using spectral reflectances obtained by measurement.

(12) The twelfth feature of the present invention resides in a color measuring method for printed matter including the tenth or eleventh feature, wherein:
in a process of computation in the fourth step, corrections based on the differential components Fp (X), Fp (Y), and Fp(Z) are not performed on an ink-adhered region within the region to be measured.

(13) The thirteenth feature of the present invention resides in a color measuring method for printed matter including the twelfth feature, wherein:
in the third step, XYZ tristimulus values Rt(X, S), Rt(Y, S), and Rt(Z, S) under the first illumination environment is measured for a region to be measured, a ratio of an area of an ink-adhered region to an entire area in the region to be measured being S;
in the fourth step, computations using the following equations:

$$Rtu(X, S) = Rt(X, S) + Fp(X) \cdot (1-S)^2$$

$$Rtu(Y, S) = Rt(Y, S) + Fp(Y) \cdot (1-S)^2$$

$$Rtu(Z, S) = Rt(Z, S) + Fp(Z) \cdot (1-S)^2$$

are performed to determine estimated XYZ tristimulus values Rtu(X, S), Rtu(Y, S), and Rtu(Z, S), under the second illumination environment, for the region to be measured.

(14) The fouteenth feature of the present invention resides in a color measuring method for printed matter including the tenth or eleventh feature, wherein:
in a process of computation in the fourth step, corrections based on the differential components Fp(X), Fp(Y), and Fp(Z) are performed in accordance to an optical transmittance of an ink layer for an ink-adhered region in the region to be measured.

(15) The fifteenth feature of the present invention resides in a color measuring method for printed matter including the fourteenth feature, wherein:
in the third step, XYZ tristimulus values Rt(X, S), Rt(Y, S), and Rt(Z, S) under the first illumination environment is measured for a region to be measured, a ratio of an area of an ink-adhered region to an entire area in the region to be measured being S;
in the fourth step, an excitation coefficient CE and a luminescence coefficient CL are defined, the excitation coefficient CE indicating a proportion of "total amount of excitation energy supplied to an ink-adhered part" per unit area with respect to "total amount of excitation energy supplied to a non-ink-adhered part" per unit area in the case where the parts are illuminated under the same conditions from an exterior, the luminescence coefficient CL indicating a proportion of "total amount of luminescence energy emitted from the ink-adhered part and observed" per unit area with respect to "total amount of luminescence energy emitted from the non-ink-adhered part and observed" per unit area in the case where emission of fluorescence from each of the parts occurs under the same conditions inside the paper, the excitation coefficient CE and the luminescence coefficient CL of the region to be measured are measured, and computations using the following equations:

$$RRtu(X, S) = Rt(X, S) + Fp(X) \cdot (1-S(1-CE)) \cdot (1-S(1-CL))$$

$$RRtu(Y, S) = Rt(Y, S) + Fp(Y) \cdot (1-S(1-CE)) \cdot (1-S(1-CL))$$

$$RRtu(Z, S) = Rt(Z, S) + Fp(Z) \cdot (1-S(1-CE)) \cdot (1-S(1-CL))$$

are performed to determine estimated XYZ tristimulus values RRtu(X, S), RRtu(Y, S), and RRtu(Z, S), under the second illumination environment, for the region to be measured.

(16) The sixteenth feature of the present invention resides in a color measuring method for printed matter including the fourteenth feature, wherein:
in the third step, XYZ tristimulus values under the first illumination environment are measured for a region to be measured, on which printing using a plurality of inks is performed and a total of n kinds of ink-adhered regions are formed by mixing of a first region in which only an ink of a single color is adhered and a second region in which a plurality of inks are adhered in an overlapping manner, a ratio of an area of an i-th region with respect to an entire area in the region to be measured being Si;
in the fourth step, an excitation coefficient CE and a luminescence coefficient CL are defined, the excitation coefficient CE indicating a proportion of "total amount of excitation energy supplied to an ink-adhered part" per unit area with respect to "total amount of excitation energy supplied to a non-ink-adhered part" per unit area in the case where the parts are illuminated under the same conditions from an exterior, the luminescence coefficient CL indicating a proportion of "total amount of luminescence energy emitted from the ink-adhered part and observed" per unit area with respect to "total amount of luminescence energy emitted from the non-ink-adhered part and observed" per unit area in the case where emission of fluorescence from each of the parts occurs under the same conditions inside the paper, and the excitation coefficient CE and the luminescence coefficient CL of each of the n kinds of ink-adhered regions are measured; and
in a process of computation in the fourth step, corrections based on the differential components Fp(X), Fp(Y), and Fp(Z) are performed on the n kinds of ink-adhered regions in the region to be measured in accordance to the excitation coefficients CE and the luminescence coefficients CL determined for the respective n kinds of ink-adhered regions.

(17) The seventeenth feature of the present invention resides in a color measuring method for printed matter including the fifteenth or sixteenth feature, wherein:
a spectral transmittance R(λ) of the ink-adhered part, a spectral transmittance P(λ) of the non-ink-adhered part, an excitation spectrum PE(λ) of the paper, and a luminescence spectrum PL(λ) of the paper are measured; and
the excitation coefficient CE and the luminescence coefficient CL of the ink-adhered part are determined using the following equations:

$$CE = \int R(\lambda) \cdot PE(\lambda) d\lambda / \int P(\lambda) \cdot PE(\lambda) d\lambda$$

$$CL = \int R(\lambda) \cdot PL(\lambda) d\lambda / \int P(\lambda) \cdot PL(\lambda) d\lambda.$$

(18) The eighteenth feature of the present invention resides in a color measuring device for determining a spectral reflectance, under a predetermined illumination environment, of a printed matter including a paper containing a fluorescent whitening agent, the color measuring device being comprised of:
- a spectral reflectance measuring device, which measures a spectral reflectance of an object to be measured under a first illumination environment;
- a storage unit, which stores a differential component $Fp(\lambda)$, obtained by subtracting a spectral reflectance $Pt(\lambda)$ of a specific paper under the first illumination environment from a spectral reflectance $Pu(\lambda)$ of the paper under a second illumination environment; and
- a computational processing unit, which performs a correction based on the differential component $Fp(\lambda)$ on a spectral reflectance $Rt(\lambda)$, which is measured by the spectral reflectance measuring device for a region to be measured in the printed matter including the specific paper, to compute an estimated spectral reflectance, under the second illumination environment, for the region to be measured.

(19) The nineteenth feature of the present invention resides in a color measuring devise for printed matter including the eighteenth feature, wherein:
the computational processing unit has a function of inputting an area ratio S of an ink-adhered region with respect to an entire area within the region to be measured and performs computation using the following equation on a spectral reflectance $Rt(\lambda, S)$, which has been measured for the region to be measured by the spectral reflectance measuring device;

$$Rtu(\lambda, S) = Rt(\lambda, S) + Fp(\lambda) \cdot (1-S)^2$$

so as to determine an estimated spectral reflectance $Rtu(\lambda, S)$, under the second illumination environment, of the region to be measured.

(20) The twentieth feature of the present invention resides in a color measuring devise for printed matter including the nineteenth feature, wherein:
a dot percent measuring device, which measures an area ratio S of an ink-adhered region with respect to an entire area within the region to be measured, is furthermore equipped.

(21) The twenty-first feature of the present invention resides in a color measuring devise for printed matter including the eighteenth feature, wherein:
the computational processing unit has a function of inputting, with regard to the region to be measured, an area ratio S of an ink-adhered region with respect to an entire area, an excitation coefficient CE, which indicates a proportion of "total amount of excitation energy supplied to the ink-adhered part" per unit area with respect to "total amount of excitation energy supplied to a non-ink-adhered part" per unit area in the case where the parts are illuminated under the same conditions from an exterior, and a luminescence coefficient CL, which indicates a proportion of "total amount of luminescence energy emitted from the ink-adhered part and observed" per unit area with respect to "total amount of luminescence energy emitted from the non-ink-adhered part and observed" per unit area in the case where emission of fluorescence from each of the parts occurs under the same conditions inside the paper, and performs computation using the following equation on a spectral reflectance $Rt(\lambda, S)$, which has been measured for the region to be measured by the spectral reflectance measuring device;

$$RRtu(\lambda, S) = Rt(\lambda, S) + Fp(\lambda) \cdot (1 - S(1-CE)) \cdot (1 - S(1-CL))$$

so as to determine an estimated spectral reflectance $RRtu(\lambda, S)$, under the second illumination environment, of the region to be measured.

(22) The twenty-second feature of the present invention resides in a color measuring devise for printed matter including the twenty-first feature, furthermore equipped with:
- a dot percent measuring device, which measures an area ratio S of an ink-adhered region with respect to an entire area within the region to be measured;
- a transmittance measuring device, which measures a spectral transmittance $R(\lambda)$ of an ink-adhered part in the region to be measured and a spectral transmittance $P(\lambda)$ of a non-ink-adhered part in the region to be measured; and
- a coefficient computation unit, which computes an excitation coefficient CE and a luminescence coefficient CL of the ink-adhered part, using the spectral transmittance $R(\lambda)$ and the spectral transmittance $P(\lambda)$ which have been measured by the transmittance measuring device, and an excitation spectrum $PE(\lambda)$ of the paper and a luminescence spectrum $PL(\lambda)$ of the paper in accordance to the following equations:

$$CE = \int R(\lambda) \cdot PE(\lambda) d\lambda / \int P(\lambda) \cdot PE(\lambda) d\lambda$$

$$CL = \int R(\lambda) \cdot PL(\lambda) d\lambda / \int P(\lambda) \cdot PL(\lambda) d\lambda.$$

(23) The twenty-third feature of the present invention resides in a color measuring devise for printed matter including the twenty-second feature, wherein:
a spectrofluorometer, which measures an excitation spectrum $PE(\lambda)$ of the paper and a luminescence spectrum $PL(\lambda)$ of the paper, is furthermore equipped and the coefficient computation unit uses the excitation spectrum $PE(\lambda)$ of the paper and the luminescence spectrum $PL(\lambda)$ of the paper measured by the spectrofluorometer in performing computation for determining the excitation coefficient CE and the luminescence coefficient CL.

(24) The twenty-fourth feature of the present invention resides in a color measuring devise for printed matter including the eighteenth to twenty-third features, wherein:
the computational processing unit has a function of computing XYZ tristimulus values based on a predetermined spectral reflectance and computes estimated XYZ tristimulus values, under the second illumination environment, for the region to be measured.

(25) The twenty-fifth feature of the present invention resides in a color measuring devise for printed matter including the twenty-fourth feature, wherein:
the storage unit stores the differential component $Fp(\lambda)$ in a form of XYZ tristimulus values; and
the computational processing unit performs computation using the differential component stored in the form of XYZ tristimulus values.

(26) The twenty-sixth feature of the present invention resides in a program, which makes a computer function as the computational processing unit in a color measuring device for printed matter having the eighteenth to twenty-fifty features, or a computer-readable medium that stores the program.

DESCRIPTION OF THE PREFERRED EMBODIMENTS

This invention shall now be described based on an illustrated embodiment.

<<< Section 1. The Spectral Reflectance Measurement Procedures of the Color Measuring Method by this Invention >>>

As has been described above, the reason why, depending on the illumination environment at a time of observation, correct evaluation standards of color cannot be indicated when a measurement by a prior-art measurement method is made on a printed matter, with which gradation is expressed by an area modulation method, such as offset printing, etc., is that a fluorescent whitening agent is contained in the printed paper.

Figure 1:
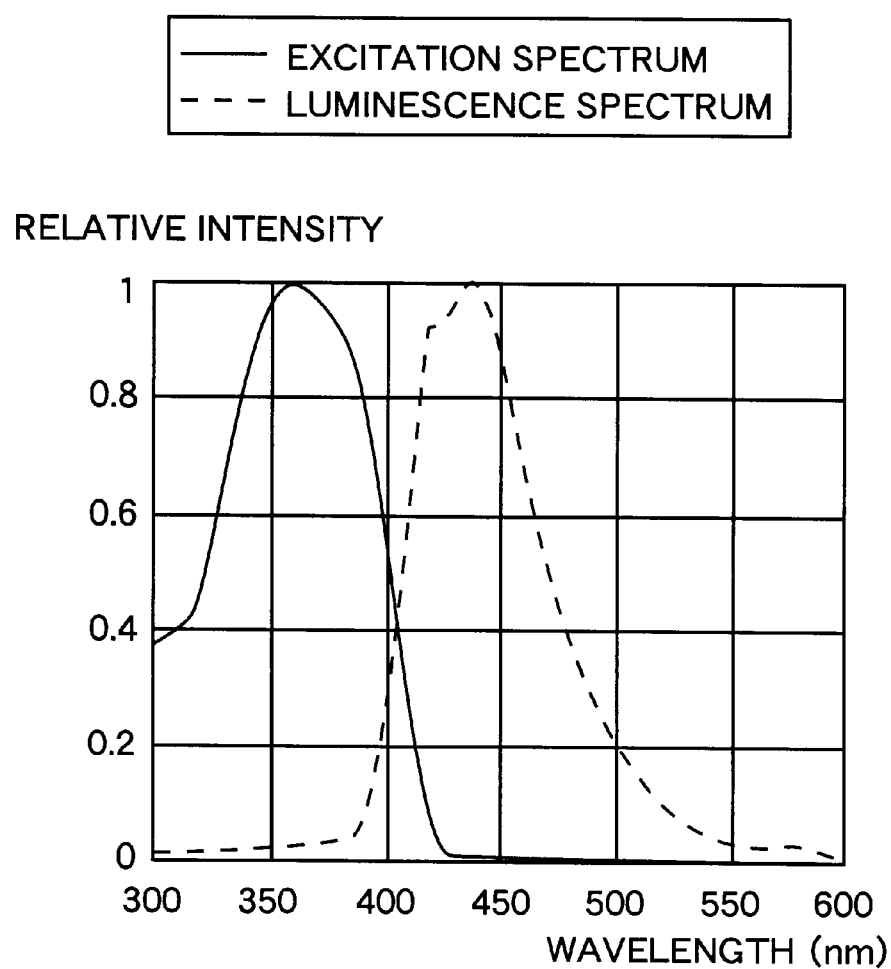
FIG. 1 shows graphs of the excitation spectrum and the luminescence spectrum of a typical fluorescent whitening agent.

FIG. 1 shows the excitation spectrum and the luminescence spectrum of a typical fluorescent whitening agent. The excitation spectrum shows a spectrum of light that is absorbed by this fluorescent whitening agent and the luminescence spectrum shows a spectrum of the fluorescence that is emitted from the fluorescent whitening agent. The fluorescent whitening agent shown here has a property of absorbing light near a wavelength of 360 nm most strongly and emitting, based on the absorbed energy, light near a wavelength of 440 nm most strongly as fluorescence. Thus when a printed paper that contains this fluorescent whitening agent is observed under the light of the abovementioned CIE standard illuminant D65, stipulated in ISO/CIE 10526, the light of a fluorescent lamp, daytime sunlight, or other light that contains a high amount of ultraviolet components, since the fluorescent whitening agent absorbs the ultraviolet components (excitation spectrum of FIG. 1) and strongly emits fluorescence in the purple to blue range (luminescence spectrum of FIG. 1), the paper will look bluish. However when the same paper is observed under illumination by a tungsten lamp or other light that is low in ultraviolet components, there will hardly be any fluorescence from the fluorescent whitening agent and the paper will thus look yellowish.

As has been mentioned above, a general color measuring device uses a tungsten lamp as the light source. Though the spectral reflectance measured by this color measuring device will thus indicate the correct color evaluation standards when a sample is illuminated by a tungsten lamp, the color evaluation standards will not be correct when the sample is illuminated by a fluorescent lamp. A basic characteristic of this invention lies in performing a process in which a correction is applied to the spectral reflectance measured using a first light source, such as a tungsten lamp, etc., to estimate the spectral reflectance when observation is made using a second light source (fluorescent lamp or daytime sunlight) that emits light containing ultraviolet components. By using this method, it becomes possible to estimate the spectral reflectance in the case where a printed matter is observed under illumination by an arbitrary light source as long as the spectral reflectance of the printed matter can be measured using a specific light source.

The basic spectral reflectance measurement procedures of the color measuring method for printed matter of this invention shall now be described based on the flowchart of FIG. 2. For the sake of convenience in the description that follows, a light source, comprised of a tungsten lamp, shall be referred to as a first light source T, a light source containing ultraviolet rays shall be referred to as a second light source U, and a description shall be given concerning an example where the spectral reflectance observed under illumination of the second light source U is estimated based on the spectral reflectance measured under illumination of the first light source T. Needless to say, the application of this invention is not limited to the case where a specific light source is used, and this invention can be applied to an arbitrary light source.

Figure 2:
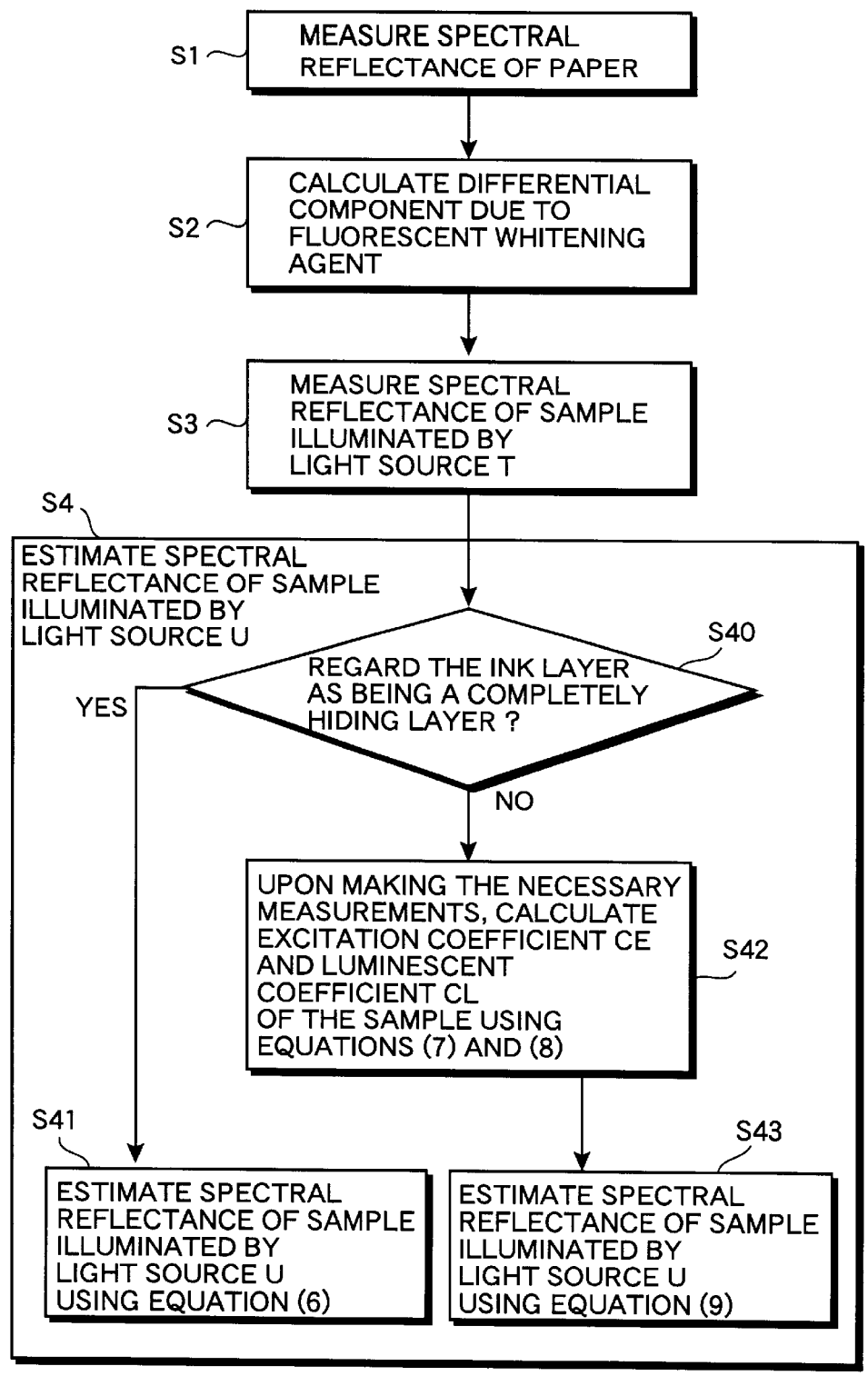
FIG. 2 is a flowchart, which shows a basic spectral reflectance measurement procedures using a color measuring method for printed matter according to this invention.

As shown in FIG. 2, the basic procedures of the color measuring method for printed matter by this invention are comprised of the four steps of measurement of the spectral reflectance of paper (step S1), calculation of the differential component due to the fluorescent whitening agent (step S2), measurement of the spectral reflectance of the sample under illumination by the first light source T (step S3), and estimation of the spectral reflectance under illumination by the second light source U (step D4). The details of these respective steps shall now be described in order.

First in step S1, a spectral reflectance of the paper is measured. The object of measurement in this step S1 is to measure a spectral reflectance of paper itself in the blank condition prior to printing. Needless to say, if there is an unprinted portion in a margin region, etc. of a printed matter, such a margin region may be used as an object of the measurement. In this step, both measurement under illumination by the first light source T and measurement under illumination by the second light source U must be made on the same paper. To be more specific, first of all, a spectral intensity distribution Pt-Raw($\lambda$) of reflected light from the paper under illumination by the first light source T is measured and a spectral intensity distribution Wt-Raw($\lambda$) of reflected light from a perfect reflecting diffuser under the same illumination is measured. Both distributions indicate the intensity values of light of wavelengths $\lambda$ and thus indicate spectra across a predetermined wavelength range. In the present specification, all variables that contain the expression ($\lambda$), signify spectra that are obtained by varying the wavelength across a predetermined wavelength range.

Likewise, a spectral intensity distribution Pu-Raw($\lambda$) of reflected light from the paper under illumination by the second light source U is measured and a spectral intensity distribution Wu-Raw($\lambda$) of reflected light from a perfect reflecting diffuser under the same illumination is measured. These measurements can be made using a general spectral radiance meter. By using these measurement results and performing the computation of equation (1) shown below, a spectral reflectance Pt($\lambda$) of the paper under illumination by the first light source T can be determined and by performing the computation of equation (2), a spectral reflectance Pu($\lambda$) of the paper under illumination by the second light source U can be determined.

$$Pt(\lambda) = Pt\text{-Raw}(\lambda)/Wt\text{-Raw}(\lambda) \qquad (1)$$

$$Pu(\lambda) = Pt\text{-Raw}(\lambda)/Wu\text{-Raw}(\lambda) \qquad (2)$$

In both of the above equations, the paper's inherent spectral reflectances Pt($\lambda$) and Pu($\lambda$), which are not affected by the spectral intensity distribution of the light source, are determined by division by the spectral intensity distribution of the reflected light from the perfect reflecting diffuser. These spectral reflectances become parameters that indicate how much light of a wavelength $\lambda$ is reflected. However, since the spectral reflectances Pt($\lambda$) and Pu($\lambda$) that are determined here contain the effects of the fluorescence that is emitted from the fluorescent whitening agent contained in the paper, Pt($\lambda$) and Pu($\lambda$) will not be equal. Correction using a perfect reflecting diffuser thus cannot eliminate the effects of the fluorescence components.

In the subsequent step S2, a differential component Fp($\lambda$), due to the fluorescent whitening agent in the paper, is computed based on equation (3).

$$Fp(\lambda) = Pu(\lambda) - Pt(\lambda) \qquad (3)$$

As has been mentioned above, the paper's spectral reflectance Pt($\lambda$) determined by equation (1) will not be equal to the paper's spectral reflectance Pu($\lambda$) determined by equation (2), because the paper contains a fluorescent whitening agent and because a difference arises in the fluorescence components that are emitted when light from the first light source T is illuminated onto the paper and the fluorescence components that are emitted when light from the second light source U is illuminated onto the paper. The spectrum of the differential component Fp($\lambda$), which is due to the fluorescent whitening agent and is determined as the difference between the above-mentioned spectra by equation (3), will thus be a parameter that indicates the difference in regard to the light sources that arises as a result of the fluorescent whitening agent.

Next in step S3, a spectral reflectance of the sample is measured under illumination by the first light source T. Here, an example shall be described where the sample is a printed matter prepared by performing offset printing onto the same paper as that which was the object of the measurement carried out in step S1. To be more specific, a procedure of determining a spectral reflectance of a printed region, which is a part of the printed matter and has a dot percent S (S=0 to 1), as the sample shall be described.

The procedure for measuring the spectral reflectance of the sample in step S3 is the same as the procedure for measuring the spectral reflectance of the paper carried out in step S1, and it is sufficient to perform the same work using the sample in place of the paper. That is, light from the first light source T is irradiated onto a specific region (a printed region of dot percent S) of the printed matter to be measured, the spectral intensity distribution Rt-Raw($\lambda$) of the reflected light obtained from this region is measured using a spectral radiance meter, and subsequently, the spectral intensity distribution Wt-Raw($\lambda$) of reflected light from a perfect reflecting diffuser is measured under the same illumination. Here, the spectral intensity distribution Wt-Raw($\lambda$) of reflected light from a perfect reflecting diffuser that was measured in step S1 may be used as it is. However, if the stability of the first light source T is not adequate and a temporal variation occurs in the spectrum of light, it is preferable to make a measurement again. By using these measurement results and performing the computation of equation (4) shown below, the spectral reflectance Rt($\lambda$, S) of the sample (printed region of dot percent S) under illumination by the first light source T can be obtained.

$$Rt(\lambda, S) = Rt\text{-Raw}(\lambda)/Wt\text{-Raw}(\lambda) \qquad (4)$$

Consequently, the measurement in step S3 is in no ways different from the prior-art measurement of the spectral reflectance using a general color measuring device and the obtained spectral reflectance Rt($\lambda$, S) will be the spectral reflectance of the sample when illuminated by a tungsten lamp. Thus when this same sample is observed under illumination by a fluorescent lamp, the spectral reflectance Rt($\lambda$, S) cannot be used as a correct color evaluation standard.

Thus in step S4, processes for estimating the spectral reflectance Ru($\lambda$, S) under illumination by the second light source U are performed. That is, in the processes in this step S4, an estimate of the spectral reflectance Ru($\lambda$, S) under illumination by the second light source U is determined through computation based on the sample's spectral reflectance Rt($\lambda$, S) under illumination by the first light source T, which was measured in step S3.

As shown in the flowchart of FIG. 2, step S4 is comprised of several sub-steps S40 to S43. This is because different processes must be performed according to whether or not the ink layer that has been adhered onto the sample printed matter is regarded as being a perfectly hiding layer. To be more specific, in step S40, it is selected whether or not the ink layer is to be regarded as being a perfectly hiding layer, and whereas in the case where the ink layer is regarded as being a perfectly hiding layer, the process of step S41 is performed, in the case where it is considered that light is transmitted through the ink layer, the processes of steps S42 and S43 are performed.

Here the process in the case where the ink layer is regarded and handled as being a perfectly hiding layer, that is, the process of step S41, shall be described first. First, in order to facilitate the comprehension of the process, the computations to obtain a correct color evaluation standard are considered in the case where blank paper (unprinted paper) is observed by a light source that differs from that used in color measurement. As has been mentioned in the description of step S1, the spectral reflectance Pt($\lambda$) of a specific paper under illumination by the first light source T can be determined by applying equation (1) to the measured values concerning the paper and a perfect reflecting diffuser.

However, when this paper is observed under illumination by the second light source U, the spectral reflectance $Pt(\lambda)$ that was determined by the measurement will no longer provide a correct color evaluation since the effects of the fluorescence components due to the fluorescent whitening agent contained in the paper will be different.

To be more specific, even if the spectral reflectance $Pt(\lambda)$ of the paper that has been obtained by measurement using a tungsten lamp (first light source T) indicates yellowish color characteristics, when this paper is observed under illumination by a fluorescent lamp (second light source U), since the differential component $Fp(\lambda)$, which is due to the fluorescent whitening agent and has been determined in step S2, will be overlapped, the components in the wavelength range of 400 to 500 nm will be strengthened and the paper will appear to have a bluish tint. Thus theoretically, by performing a correction of adding the differential component $Fp(\lambda)$ due to the fluorescent whitening agent to the paper's spectral reflectance $Pt(\lambda)$ that was obtained by measurement using the tungsten lamp, the spectral reflectance $Pu(\lambda)$ that will be obtained by measurement of this paper under illumination by the fluorescent lamp can be determined by computation. Since the spectral reflectance $Pu(\lambda)$ that has been determined in this manner will not be an actually measured reflectance but will be an estimate determined by computation using the measured values of $Pt(\lambda)$, it shall be indicated here as $Ptu(\lambda)$. Here, the suffix tu indicates the reflectance values as being "estimated values under the second light source U" determined by computation using "measured values under the first light source T."

The estimated spectral reflectance $Ptu(\lambda)$ of the paper under illumination by the second light source U is thus determined based on the measured spectral reflectance $Pt(\lambda)$ of the paper under illumination by the first light source T by performing the computation of equation (5).

$$Ptu(\lambda)=Pt(\lambda)+Fp(\lambda) \tag{5}$$

Here, $Fp(\lambda)$ is the differential component due to the fluorescent whitening agent and is the spectrum that is obtained by equation (3) in step S2.

As the equation (5) given above is an equation that can be applied to blank paper on which no printing whatsoever has been performed, this equation (5) cannot be applied as it is to a printed matter on which printing has actually been performed. However, in the case where the ink layer is considered to be a perfectly hiding layer, it becomes possible to apply equation (6), which is obtained by slight modification of equation (5), to the printed matter.

$$Rtu(\lambda, S)=Rt(\lambda, S)+Fp(\lambda)\cdot(1-S)^2 \tag{6}$$

Here, $Rt(\lambda, S)$ is the spectrum determined by the computation of equation (4) in step S3 and is the measured spectral reflectance of the sample (printed region of dot percent S) under illumination by the first light source T. $Fp(\lambda)$ is the spectrum of the differential component due to the fluorescent whitening agent that was determined using equation (3) in step S2. S is the dot percent of the sample. $Rtu(\lambda, S)$ that is determined by the computation of this equation (6) is the estimated spectral reflectance of the sample under illumination by the second light source U.

A comparison of equation (6) with equation (5) shows that the two are the same except for the $(1-S)^2$ term. That is, basically, the correction of adding the differential component $Fp(\lambda)$, due to the fluorescent whitening agent, to the measured spectral reflectance $Rt(\lambda, S)$ of the sample under illumination by the first light source T is performed.

However, the differential component $Fp(\lambda)$, due to the fluorescent whitening agent, is multiplied by the term, $(1-S)^2$. This is because whereas equation (5) is an equation that is applied to blank paper, equation (6) is an equation that is applied to a sample (printed matter) onto which ink has been adhered. The numerical value S (S=0 to 1) is the dot percent of the sample and is a parameter that indicates the proportion of the area of the ink-adhered part with respect to the total area of the measured region, which is the sample. For example, if S=0, no ink whatsoever has been adhered onto the measured region, if S=1, the entirety of the measured region is covered by ink, and if S=0.5, the total area of the part within the measured region that is covered by ink is half the entire area. Here, since the ink layer is considered as being a perfectly hiding layer, light from a light source does not reach a surface of the paper at the part onto which ink has been adhered, and even if fluorescence is emitted from the paper, the fluorescence that has been emitted from the paper will not be emitted to the exterior at the part onto which ink has been adhered.

In order for the fluorescent whitening agent contained in the paper to emit fluorescence, first, the energy for causing fluorescence must be supplied from the exterior. In order to supply energy for luminescence, the light (light of the wavelength range of the excitation spectrum of FIG. 1) from the light source must reach the molecules of the fluorescent whitening agent in the interior of the paper. However, at a part where an ink layer that functions as a hiding layer is formed on the paper, the energy of light from the light source will not reach the fluorescent whitening agent. In the case of a sample with a dot percent S, a part corresponding to the proportion S among the entire measured region is covered by the ink layer. Therefore, among the entire light energy from the light source, only that which is irradiated onto the part corresponding to the proportion (1−S) of the entire region (the part at which the bare surface of the paper is exposed) reaches the fluorescent whitening agent. Consequently, if 1 is the amount of light energy that is supplied to the fluorescent whitening agent of a sheet of blank paper with which no ink layer is formed on the surface, the amount of light energy that is supplied to the fluorescent whitening agent contained in a sample of dot percent S will be (1−S).

Meanwhile, even if some energy is supplied from the exterior to the fluorescent whitening agent contained in the paper and fluorescence (light of the wavelength range of the luminescence spectrum of FIG. 1) is emitted from the fluorescent whitening agent due to this energy, this fluorescence must reach an observer in order for it to be observed. However, at a part where an ink layer that functions as a hiding layer is formed on the paper, the fluorescence that is emitted from the fluorescent whitening agent will not reach the exterior. Consequently, if 1 is the intensity of fluorescence that is emitted to the exterior from a sheet of blank paper with which no ink layer is formed on the surface, the intensity of fluorescence that is emitted to the exterior from a sample of dot percent S will be (1−S).

In equation (6), the differential component $Fp(\lambda)$ which is a correction term due to the fluorescent whitening agent is multiplied by the squared term $(1-S)^2$. This is because the amount of energy supplied to the fluorescent whitening agent from an external light source is attenuated to (1−S) and the amount of fluorescence that has been generated in the interior and reaches the exterior is attenuated to (1−S). That is, in the case of a sample with a dot percent S, since the amount of energy supplied to the fluorescent whitening agent decreases to (1−S) and the amount of fluorescence that is emitted to the exterior also decreases to (1−S) in comparison to blank paper, the intensity of fluorescence that finally reaches an observer will be $(1-S)^2$. Here the factor (1−S), which indicates the efficiency of excitation of the fluorescent whitening agent by an external light source, and the factor (1−S), which indicates the efficiency of emission to the exterior of the fluorescence that has been generated in the interior, must be multiplied since the excitation energy that is supplied to the interior of the paper is diffused in the interior of the paper and it is thus considered that excitation of molecules of the fluorescent whitening agent occurs even at parts that are covered by the ink layer. The factor (1−S), which indicates the efficiency of excitation of the fluorescent whitening agent by an external light source, and the factor (1−S), which indicates the efficiency of emission to the exterior of the fluorescence that has been generated in the interior, are factors that respectively concern separate, independent physical phenomena and the value of $(1-S)^2$, obtained by multiplying these factors, must be used as the factor that indicates the efficiency at which the fluorescence components reach an observer in the final stage.

It can be understood from a consideration of the above-described phenomena that by applying equation (6) to a sample comprised of a printed matter, the estimated spectral reflectance Rtu ($\lambda$, S) of the sample under illumination by the second light source U can be determined. However, the following conditions must be satisfied in order to apply equation (6) to a sample. That is, the printed matter must be a printed matter with which gradation is expressed by an area modulation method, such as offset printing, etc., and must be a printed matter for which it is feasible to handle the ink layer as a perfectly hiding layer. Here, that "the ink layer can be feasibly handled as a perfectly hiding layer" signifies that the ink layer is comparatively low in transmittance of light in the effective wavelength range (range of approximately 300 to 500 nm) of the excitation spectrum and luminescence spectrum of the fluorescent whitening agent that is contained in the paper.

For example, in the case of a printed matter that has been printed with black ink, the light irradiated onto an ink-adhered part of the paper is mostly absorbed within the ink layer and hardly reaches the bare surface of the paper. Also, even if a small amount of light reaches the bare surface of the paper, the fluorescence emitted from the paper will not be transmitted through the ink layer again and will not reach the exterior. Thus a printed matter that has been printed with black ink will be a "printed matter for which it is feasible to handle the ink layer as a perfectly hiding layer." Equation (6) can also be applied in the case where the sample is a printed matter of multiple colors in which a plurality of types of ink layers, which can be feasibly handled as perfectly hiding layers, such as ink layers of black ink and dark brown ink, are formed. In this case the total of the respective dot percents of the plurality of inks can be used as S.

Needless to say, for practical purposes, even in the case where an ink layer that transmits light to some degree is formed, the ink layer may be handled as a perfectly hiding layer and equation (6) may be applied. Even in cases where the ink layer is not a perfectly hiding layer, equation (6) can still be used to calculate effective estimates. However, the accuracy of the estimate that is obtained will be low in comparison to the case where the below-described processing method of steps S42 and S43 is employed. That is, the judgment of step S40 of FIG. 2 may be made based on an arbitrary judgment by the measurer. Needless to say, the judgment of step S40 can also be made objectively by actually measuring the optical transmittance of the ink layer of the sample and comparing the measured values with predetermined reference values.

The dot percent S of the sample can be measured by using a dot percent meter. Or, if the DTP (Desk Top Publishing) data, used in preparing the printed matter, is available for use, the information on the dot percent of the sample may be acquired directly from the DTP data. In this invention, the numerical value S does not necessarily have to be the area percent of halftone dots, and any area percent may be used as long as it indicates the proportion of the area of the ink-adhered part with respect to the total area of the measured region that is the sample in the printed matter on which gradation is expressed by an area modulation method. However for the sake of convenience, in the description of the embodiment of this invention, an example where the numerical value S is a dot percent shall be described.

Next, the case where the ink layer is not regarded as being a perfectly hiding layer in step S40 of the flowchart of FIG. 2 shall be described. In this case, the processes of steps S42 and S43 are performed. As has been mentioned above, the case where the ink layer is regarded as being a perfectly hiding layer can be handled without considering the effects of the fluorescence components that are emitted from the fluorescent whitening agent in the ink-adhered part. However, in the case where the ink layer is not regarded as being a perfectly hiding layer, light from the light source is regarded to be transmitted through the ink layer and supplies energy to the fluorescent whitening agent, and the fluorescence that has been emitted as a result of the supplied energy is regarded to be transmitted through the ink layer and emitted to the exterior. The influence of the fluorescence components must thus be taken into consideration in accordance with the transmittance of the ink layer in the ink-adhered part as well. As has been mentioned above, though the judgment of step S40 can be made based on an arbitrary judgment by the measurer, when color measurement is to be performed for a sample having an ink layer which is comparatively low in the property of hiding light in the short wavelength range, such as an ink layer of cyan, magenta, etc., an estimate of higher accuracy can be obtained by regarding the ink layer as not being a perfectly hiding layer.

Figure 3:
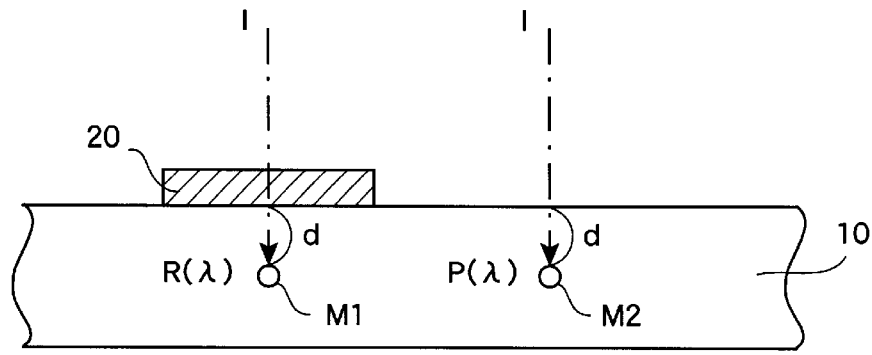
FIG. 3 is a sectional side view, which illustrates the fluorescence process in the case where an ink layer 20, with some degree of light transmittance, is formed on a part of the surface of a paper 10.

Referring to the sectional side view of FIG. 3, a fluorescence process shall now be considered. In the case shown in FIG. 3, an ink layer 20 that transmits light to some degree is formed on a part of the surface of a paper 10. Here, the process of excitation of a molecule M1 and a molecule M2 of the fluorescent whitening agent which exists inside paper 10 shall be considered. Here, each of molecules M1 and M2 can be considered to be an arbitrary molecule that is positioned at a standard depth d that is suited for excitation from the surface of the paper. In order to excite molecule M1 or M2, energy of light I from the exterior must reach the position of molecule M1 or M2 and must be absorbed by molecule M1 or M2.

For the sake of explanation, a spectral transmittance R($\lambda$) of the ink-adhered part and a spectral transmittance P($\lambda$) of the non-ink-adhered part shall be defined. R($\lambda$) is a parameter that indicates the proportion of attainment of light I from the exterior to the position of molecule M1 for each wavelength $\lambda$. For example, if the intensity of the component of wavelength $\lambda i$ contained in the light I is 100% and the intensity of the component of wavelength $\lambda i$ that has reached the position of molecule M1 is 30%, R($\lambda i$)=0.3. In this case, 70% of the component of wavelength $\lambda i$ is absorbed by ink layer 20 or paper 10 (if reflection at the interface of the layer is not considered). Likewise, P($\lambda$) is a parameter that indicates the proportion of attainment of light I from the exterior to the position of molecule M2 for each wavelength $\lambda$. Though both R($\lambda$) and P($\lambda$) are data obtained as spectra and indicate the transmittance for each wavelength, the former is the spectral transmittance through ink layer 20 and a portion of thickness d in paper 10 and the latter is the spectral transmittance through just the portion of thickness d in paper 10. Obviously, due to the existence of the ink layer 20, R($\lambda$)<P($\lambda$).

Here, not all of the energy of the light that has reached the molecule M1 or M2 is used as excitation energy. The proportion of the light energy of each wavelength that is used as excitation energy is determined based on the excitation spectrum shown in FIG. 1. If the excitation spectrum of the paper 10 is expressed by PE($\lambda$), the total amount of energy that is absorbed and used by molecule M1 is determined by integration over the entire wavelength range and is expressed by the integral value $\int R(\lambda) \cdot PE(\lambda) d\lambda$. For example, the component of wavelength $\lambda i$ that reaches the position of molecule M1 is R($\lambda i$) and the proportion of this that is absorbed by molecule M1 is PE($\lambda i$). Consequently, the proportion of the energy which is absorbed by molecule M1 among the entire energy of the component of wavelength $\lambda i$ contained in the light I that is irradiated from the exterior, is R($\lambda i$)·PE($\lambda i$). Thus by integrating this over the entire wavelength range, the above-mentioned integration value is obtained and the total amount of energy that is absorbed and used by molecule M1 is thus determined. It is to be noticed that PE($\lambda$) is not the excitation spectrum of the fluorescent whitening agent, but the excitation spectrum of paper 10. This is because the paper 10 normally contains various fluorescent molecules besides the fluorescent whitening agent. PE($\lambda$) is thus the excitation spectrum of all of the fluorescent materials, including the fluorescent whitening agent, that are contained in paper 10.

In exactly the same manner, the total amount of energy that is absorbed and used by molecule M2 is determined by integration over the entire wavelength range and is expressed by the integral value $\int P(\lambda) \cdot PE(\lambda) d\lambda$. Consequently, the total amount of energy that is supplied to the molecule M1 of the ink-adhered part is determined by the integral value $\int R(\lambda) PE \cdot PE(\lambda) d\lambda$, and the total amount of energy supplied to the molecule M2 of the non-ink-adhered part is determined by the integral value $\int P(\lambda) \cdot PE(\lambda) d\lambda$. Here, if the excitation coefficient CE concerning the ink-adhered part is defined as a proportion of the "total amount of excitation energy supplied to the ink-adhered part" per unit area with respect to the "total amount of excitation energy supplied to the non-ink-adhered part" per unit area when both parts are illuminated from the exterior under the same conditions, the following equation (7) holds:

$$CE = \int R(\lambda) \cdot PE(\lambda) d\lambda / \int P(\lambda) \cdot PE(\lambda) d\lambda \quad (7)$$

That is, this excitation coefficient CE is a parameter that indicates what proportion of the excitation energy is supplied to molecule M1 with respect to molecule M2 when light I from the exterior is irradiated under the same conditions onto a region in which the ink layer 20 is formed (the region in which molecule M1 exists) and a region in which the ink layer 20 is not formed (the region in which molecule M2 exists) as shown in FIG. 3.

Next, the proportion of the emission energy that reaches an observer, in the case where it is assumed the fluorescence of the same energy is emitted from each of the molecules M1 and M2 in the sectional side view of FIG. 3, shall be considered. For this, the luminescence coefficient CL concerning the ink-adhered part is defined as the proportion of the "total amount of luminescence energy emitted from the ink-adhered part" per unit area with respect to the "total amount of luminescence energy emitted from the non-ink-adhered part" per unit area when the emission of fluorescence occurs under the same conditions for both parts inside the paper. The following equation (8) then holds:

$$CL = \int R(\lambda) \cdot PL(\lambda) d\lambda / \int P(\lambda) \cdot PL(\lambda) d\lambda \quad (8)$$

Here, as has been mentioned above, R($\lambda$) and P($\lambda$) are the spectral transmittances of the ink-adhered part and non-ink-adhered part, respectively. Also, PL($\lambda$) is the luminescence spectrum of paper 10, and is thus the luminescence spectrum of all fluorescent materials including the fluorescent whitening agent, that are contained in paper 10. Whereas equation (7) indicates the transmittance efficiency of the ink layer with regard to the energy that is supplied from the exterior to the interior of the paper 10, equation (8) indicates the transmittance efficiency of the ink layer with regard to the energy that is emitted from the interior of the paper 10 to the exterior.

That is, considering the region in which the ink layer 20 is formed (the region in which the molecule M1 exists) and the region in which the ink layer 20 is not formed (the region in which the molecule M2 exists) as shown in FIG. 3, the luminescence coefficient CL is a parameter that indicates what proportion of the energy emitted from the molecule M1 in comparison to the energy emitted from the molecule M2 reaches an observer when fluorescence of exactly the same energy is emitted from each of molecules M1 and M2.

In the process of step S42 shown in the flowchart of FIG. 2, the excitation coefficient CE of the sample is calculated based on equation (7) and the luminescence coefficient CL of the sample is calculated based on equation (8). In order to perform these calculations, the excitation spectrum PE($\lambda$) of the paper, the luminescence spectrum PL($\lambda$) of the paper, the spectral transmittance R($\lambda$) of the ink-adhered part, and the spectral transmittance P($\lambda$) of the non-ink-adhered part must be determined. With regard to the computation of integrating with respect to the wavelength $\lambda$, it is sufficient for practical purposes to perform the computation of integration over the range of approximately 300 to 780 nm. It is thus sufficient to measure the above-mentioned spectra, PE($\lambda$), PL($\lambda$), R($\lambda$), and P($\lambda$), across the wavelength range of approximately 300 to 780 nm.

The excitation spectrum PE($\lambda$) of the paper and the luminescence spectrum PL($\lambda$) of the paper can be measured by a known method using a spectrofluorometer or other device. The values of these spectra may be measured for the same paper as the paper used in the printed matter that is the sample or may be measured using a margin part, etc. of the printed matter that is the sample.

Figure 5:
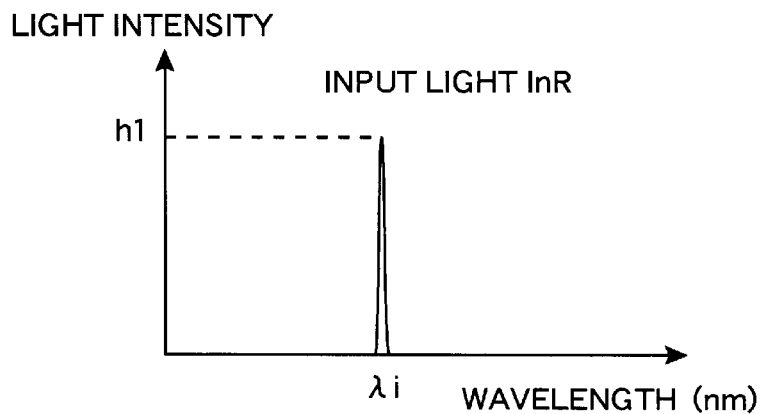
FIG. 5 is a diagram, which shows an example of a spectrum of an input light InR of FIG. 4.
Figure 6:
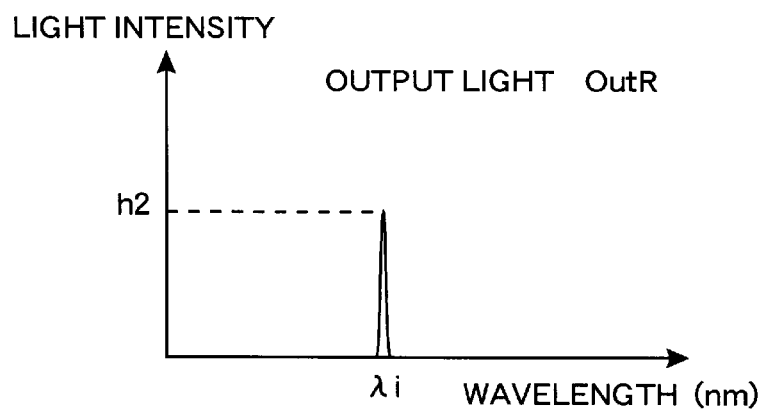
FIG. 6 is a diagram, which shows an example of a spectrum of an output light OutR of FIG. 4.

Meanwhile, the spectral transmittance R($\lambda$) of the ink-adhered part and the spectral transmittance P($\lambda$) of the non-ink-adhered part can, in principle, be measured by carrying out the following measurement using the printed matter that is the sample. Supposing that an ink layer 20, with a light-transmitting property, is formed on a part of the surface of paper 10 as shown in the left half of the sectional side view of FIG. 4, a predetermined input light InR is irradiated from above to the ink layer 20 as illustrated, and an output light OutR which has passed though the ink layer 20 and the paper 10 is observed below. Here, the input light InR is made to be a monochromatic light of a single, specific wavelength $\lambda i$. Since it is actually difficult to prepare an input light InR with a line spectrum of a single wavelength $\lambda i$, it is sufficient to irradiate light having a steep peak at the position of the single wavelength $\lambda i$ as shown in the spectrum of FIG. 5 as the input light InR. Here, suppose that when such an input light InR has been irradiated from above, the output light OutR, with the spectrum shown in FIG. 6, is obtained below. In this case, when the intensity value h1 of the wavelength λi of the input light InR shown in FIG. 5, and the intensity value h2 of the wavelength λi of the output light OutR shown in FIG. 6 are measured so that the value of the ratio h2/h1 can be obtained, the obtained value h2/h1 indicates the spectral transmittance R(λi) for the light of wavelength λi at the ink-adhered part (which is not just the ink layer 20 but is the part that includes the paper 10 below the ink layer). In other words, since light of a wavelength value λi and intensity value h1, which has been irradiated from above, is attenuated in intensity value to h2 by transmission through the ink-adhered part, the transmittance for wavelength λi is expressed as h2/h1.

By repeating such a measurement across the entire wavelength range that is required, the spectral transmittance R(λ) of the ink-adhered part can be determined. Likewise, for the non-ink-adhered part shown in the right half of the sectional side view of FIG. 4, by repeating the measurement, wherein an input light InP with a predetermined single wavelength is irradiated from above as illustrated and an output light OutP that is passed through the bottom is observed, over the entire required wavelength range, the spectral transmittance P(λ) of the non-ink-adhered part can be determined.

Figure 4:
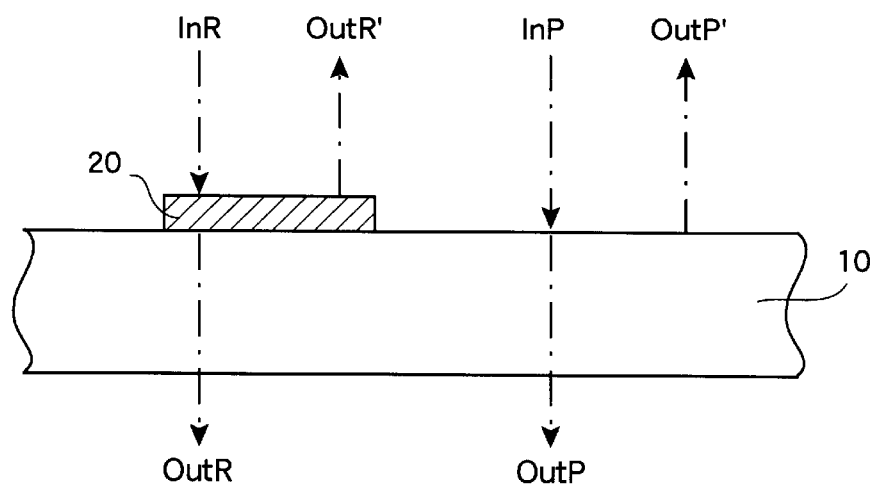
FIG. 4 is a sectional side view, which explains the principle of measurement of the spectral transmittance $R(\lambda)$ of an ink-adhered part and the spectral transmittance $P(\lambda)$ of a non-ink-adhered part.

However, in actuality, it is difficult to measure the output light OutR or OutP that is transmitted and emitted from the bottom of paper 10 as shown in FIG. 4. This is because a generally-used paper 10 is considerably low in light transmission and the transmitted light that is emitted below will be considerably attenuated in intensity. Thus for practical purposes, the output light OutR' and OutP', which is emitted upwards, may be measured in place of measuring the output light OutR and OutP. Since in the process of transmitting through the ink layer 20 and the interior of paper 10, the irradiated input light InR becomes absorbed gradually while being reflected and scattered repeatedly, output light OutR' and OutP' is observed from the upper side as well. Moreover, it is known that the intensity values of the output lights OutR' and OutP' is substantially proportional to the intensity values of the output lights OutR and OutP and can thus be substituted as the intensity values of the output lights OutR and OutP.

Figure 7:
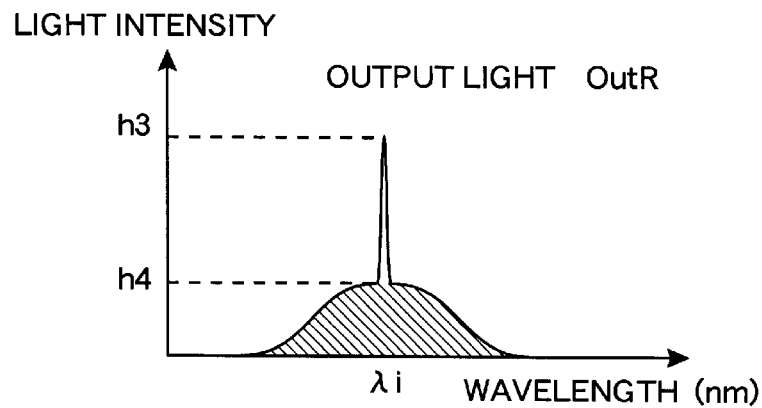
FIG. 7 is a diagram, which shows an example of a spectrum that contains the fluorescent component of the output light OutR of FIG. 4.

Also, in determining the spectral transmittance R(λ) of the ink-adhered part and the spectral transmittance P(λ) of the non-ink-adhered part by the above-described method, values that are not affected by fluorescence must be determined. That is, the fluorescent whitening agent that is contained in paper 10 will be excited by light in the short wavelength range and emit fluorescence. Since this fluorescence component is a component that is to be eliminated in the process of measuring the transmittance of light, if the output lights OutR, OutP, OutR', and OutP' contain fluorescence components, a process of determining the intensity values upon elimination of these components must be performed. For example, if for the input light InR shown in FIG. 5, the output light OutR shown in FIG. 7 is obtained, since the hatched part spanning across a broad wavelength range is a fluorescence component, the value obtained by subtracting the intensity value h4 of the fluorescence component from the output intensity value h3, in other words, a value of h3−h4 must be used as the output light intensity of wavelength λi.

As has been described above, since the excitation spectrum PE(λ) of the paper, the luminescence spectrum PL(λ) of the paper, the spectral transmittance R(λ) of the ink-adhered part, and the spectral transmittance P(λ) of the non-ink-adhered part can all be determined by measurements, the excitation coefficient CE of the sample can be calculated based on equation (7) and the luminescence coefficient CL of the sample can be calculated based on equation (8). The process of step S42 shown in the flowchart of FIG. 2 is a process wherein such measurements and calculations are performed.

Lastly in step S43, the process of computing the spectral reflectance RRtu (λ, S) of the sample under illumination by the second light source U by using equation (9) is performed.

$$RRtu(\lambda, S) = Rt(\lambda, S) + Fp(\lambda) \cdot (1 - S(1-CE)) \cdot (1 - S(1-CL)) \qquad (9)$$

Here, Rt(λ, S) is the spectrum determined by the computation of equation (4) in step S3 and is the measured spectral reflectance of the sample (the printed region of dot percent S) under illumination by the first light source T. Also, Fp(λ) is the spectrum of the differential component due to the fluorescent whitening agent, which was determined by equation (3) and S is the dot percent. Though the Rtu(λ, S), determined by the computation of the above-described equation (6), and the RRtu(λ, S), determined by the computation of the above equation (9), are the same in that both are spectral reflectances of the sample under illumination by the second light source U, whereas the values of the former are calculated by handling the ink layer as a perfectly hiding layer, the values of the latter are calculated by considering that the ink layer transmits light.

A comparison of equation (6) and equation (9) shows that the only point of difference is that the term $(1-S)^2$ in the former equation is replaced by the term $(1-S(1-CE)) \cdot (1-S(1-CL))$ in the latter equation. This is because whereas in the former case, the region of dot percent S was handled as being hidden completely, in the latter case, the region is handled as follows. That is, of the light that supplies excitation energy from the exterior, a proportion corresponding to the excitation coefficient CE is transmitted through the ink layer even in the ink-adhered part, which corresponds to a dot percent of S, so that the effective value of contribution to hiding of the dot percent will be S(1−CE). Likewise, of the emission energy that is emitted to the exterior, a proportion corresponding to the luminescence coefficient CL is transmitted through the ink layer even in the ink-adhered part, which corresponds to a dot percent of S, so that the effective value of contribution to hiding of the dot percent will be S(1−CL). From the above reasons, it can be understood that by applying equation (9) to the sample, comprised of printed matter, the estimated spectral reflectance RRtu(λ, S) under illumination by the second light source U, which takes into consideration even the light that is transmitted through the ink layer, is determined.

Figure 8:
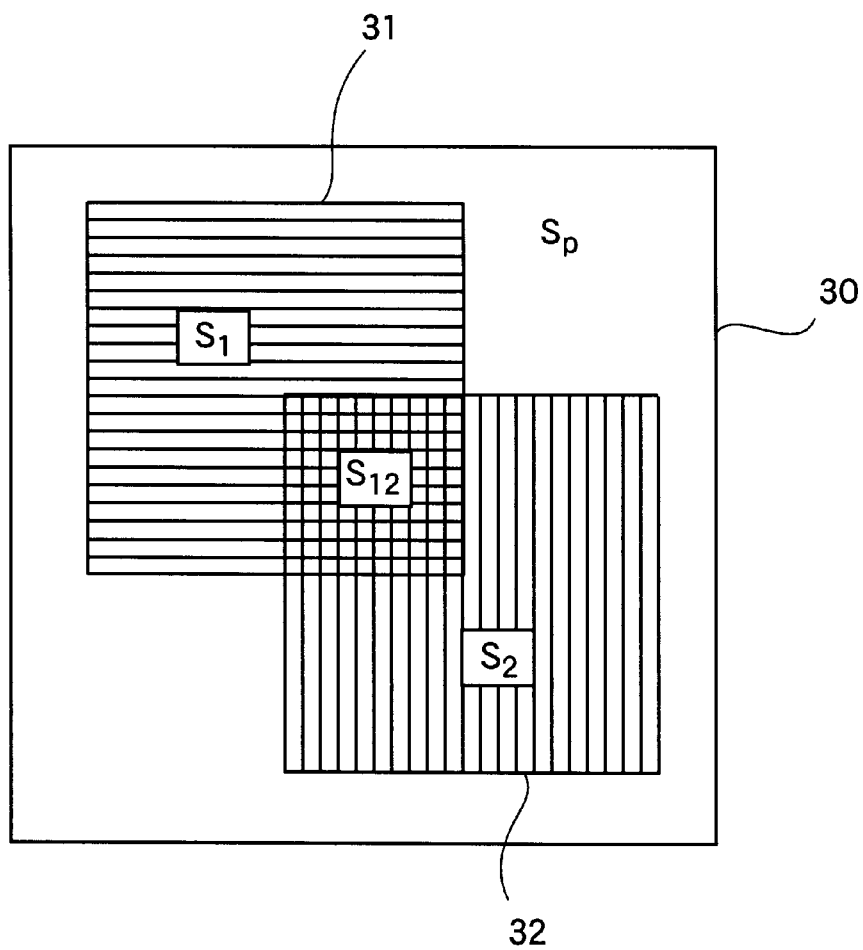
FIG. 8 is a plan view, which shows the halftone dots of a sample for explaining the handling of the case where halftone dots due to a plurality of inks overlap.

Lastly, the handling of the case where dots of plurality of inks are overlapped shall be discussed. Consider for example the case where, as shown in FIG. 8, a first halftone dot 31 (the square part indicated by horizontal hatching) and a second halftone dot 32 (the square part indicated by vertical hatching) exist in a partially overlapped manner in a sample 30 (the partial region that is to be measured in the printed matter). Actually, though the situation where only two such halftone dots exist as illustrated in the measured sample is unlikely, here it shall be considered, for the sake of convenience, that just two halftone dots 31 and 32, each of a different type of ink, exist as shown in FIG. 8. Halftone dot 31 is a part with which an ink layer of a first ink is adhered onto the paper and halftone dot 32 is a part with which an ink layer of a second ink is adhered onto the paper.

Here, with 1 being the entire area of sample 30, let $S_1$ be the area of the region in which only the first ink has been adhered, $S_2$ be the area of the region in which only the second ink has been adhered, $S_{12}$ be the area of the region in which both inks have been adhered in an overlapping manner, and $S_p$ be the area of the region in which none of the inks have been adhered. In this case, the following equation holds for the areas within sample 30.

$$1-S_p = S_1 + S_2 + S_{12} \quad (10)$$

In this case, the estimated spectral reflectance $RRtu(\lambda, S_1, S_2, S_{12})$ of sample 30 under illumination by the second light source U, with which even the light that is transmitted through the ink layer is considered, can be calculated using equation (11).

$$RRtu(\lambda, S_1, S_2, S_{12}) = Rt(\lambda, S_1, S_2, S_{12}) + Fp(\lambda) \cdot (S_p + S_1 \cdot CE_1 + S_2 \cdot CE_2 + S_{12} \cdot CE_{12}) \cdot (S_p + S_1 \cdot CL_1 + S_2 \cdot CL_2 + S_{12} \cdot CL_{12}) \quad (11)$$

Here, $Rt(\lambda, S_1, S_2, S_{12})$ is the measured spectral reflectance of sample 30 under illumination by the first light source T. $Fp(\lambda)$ is the spectrum of the differential component due to the fluorescent whitening agent, which has been determined by equation (3) in step S2. Meanwhile, $CE_1$, $CE_2$, and $CE_{12}$ are the excitation coefficients that have been determined for the region in which only the first ink has been adhered, the region in which only the second ink has been adhered, and the region in which both inks have been adhered in an overlapping manner, respectively, and $CL_1$, $CL_2$, and $CL_{12}$ are the luminescence coefficients that have been determined for these respective regions.

Though equation (11) is applicable to a sample in which halftone dots of two types of inks have been formed as shown in FIG. 8, equations that are applicable to samples in which halftone dots of three or more types of inks have been formed can be obtained along the same line of thought. In general, in the case of a sample having halftone dots, each of which are formed from a plurality of inks, by setting the dot percents of each individual region as $S_1, S_2, \ldots, S_n$, the excitation coefficients of each region as $CE_1, CE_2, \ldots, CE_n$, and the luminescence coefficients as $CL_1, CL_2, \ldots, CL_n$ and performing a computation equivalent to equation (11), the estimated spectral reflectance of the sample under illumination by the second light source U can be determined based on the measured spectral reflection of the sample under illumination by the first light source T.

To be more specific, in the case where the sample is printed using a plurality of inks and a total of n types of ink-adhered regions are formed by the mixing of regions with which only an ink of a single color has been adhered and regions with which a plurality of inks have been adhered in an overlapping manner, the estimated spectral reflectance of the sample under illumination by the second light source U can be determined by the following method. First, in step S3, the spectral reflectance of the sample under illumination by the first light source T is measured. Next, in step S4, the excitation coefficient CE and luminescence coefficient CL are measured for each of the above-mentioned n types of ink-adhered regions, and for these n types of ink-adhered regions, correction based on the differential component $Fp(\lambda)$ is performed in accordance to the excitation coefficients CE and luminescence coefficients CL that have been determined for the respective regions.

<<< Section 2. Outline of the Procedures of the Spectral Reflectance Measurement Method Related to this Invention >>>

Figure 9:
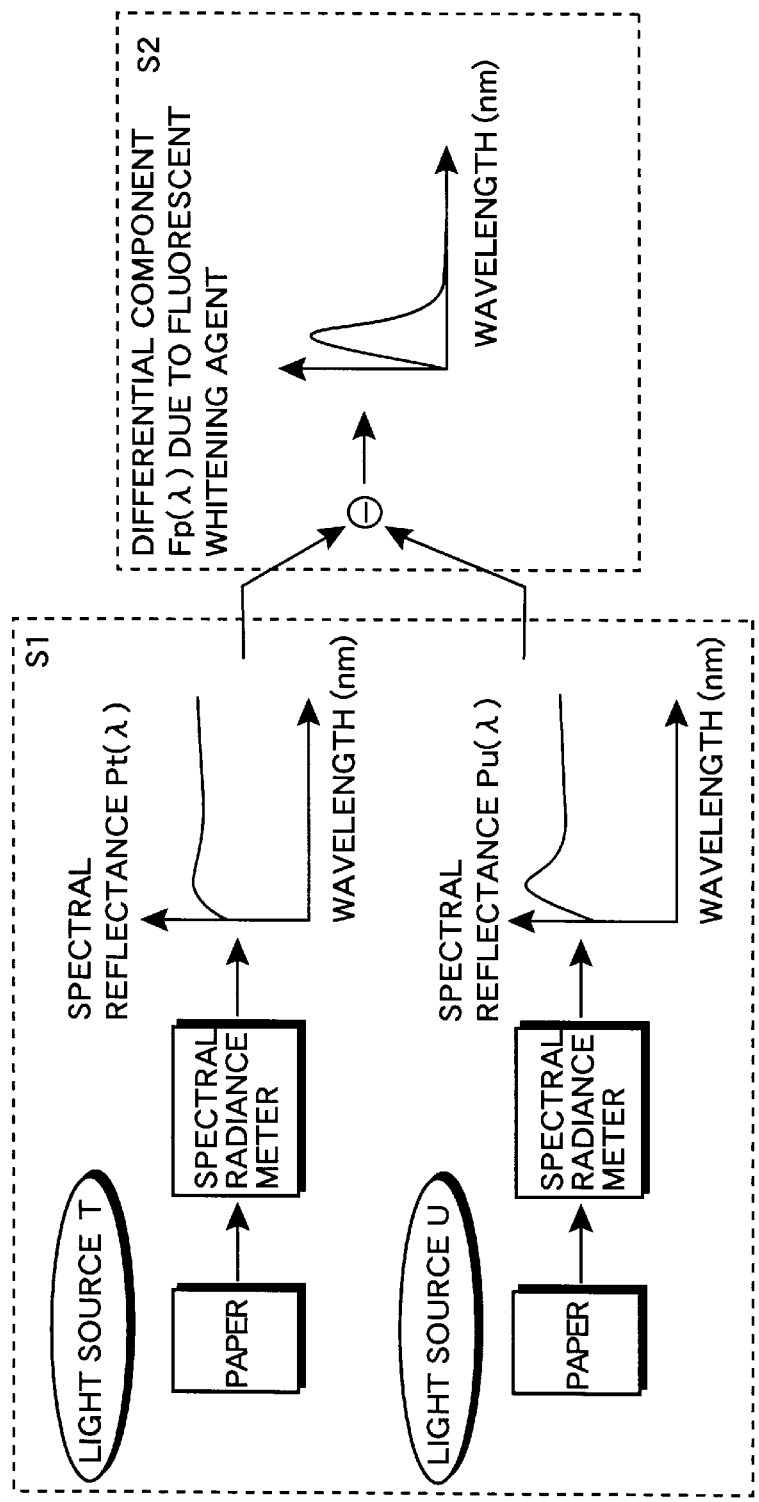
FIG. 9 is a diagram, which illustrates the procedures of steps S1 and S2 in the flowchart shown in FIG. 2.
Figure 10:
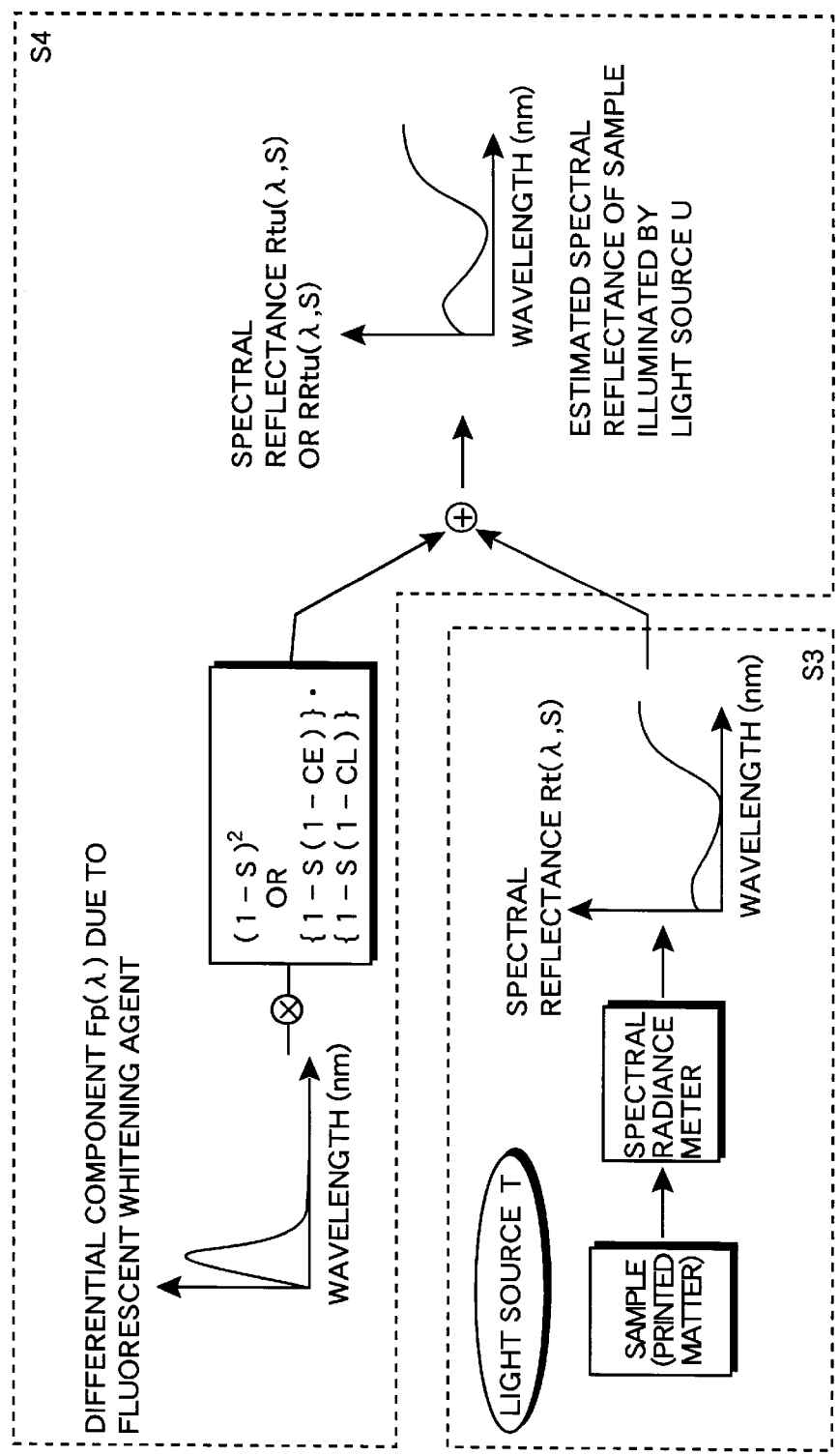
FIG. 10 is a diagram, which illustrates the procedures of steps S3 and S4 in the flowchart shown in FIG. 2.

Here, an outline of the procedures given in Section 1 shall be described briefly based on the diagrams of FIGS. 9 and 10 and the results of application to a specific printed matter shall be indicated.

FIG. 9 is a diagram, which illustrates the procedures of steps S1 and S2. First in step S1, the respective reflected light intensities under illumination by the first light source T and the second light source U are measured using a spectral radiance meter, and the spectral reflectances $Pt(\lambda)$ and $Pu(\lambda)$ are determined. In this process, the correction computations based on equations (1) and (2) are carried out using a perfect reflecting diffuser as has been mentioned above.

Next in step S2, the subtraction based on equation (3) is performed, thereby obtaining the differential component $Fp(\lambda)$ due to the fluorescent whitening agent in the paper. In the case of the example described here, since the first light source T is a tungsten lamp, which hardly contains any ultraviolet components, and the second light source U is a light source that contains a high amount of ultraviolet components, the spectrum of spectral reflectance $Pu(\lambda)$ contains more components in the wavelength range of 400 to 500 nm in comparison to the spectrum of spectral reflectance $Pt(\lambda)$ as shown in FIG. 9. This is because when illumination by the second light source U, which contains a high amount of ultraviolet components, is performed, the fluorescent whitening agent absorbs these ultraviolet components, as shown by the excitation spectrum of FIG. 1, and emits fluorescence in the wavelength range of 400 to 500 nm, as shown by the luminescence spectrum of FIG. 1. The spectrum of the differential component $Fp(\lambda)$, which is due to the fluorescent whitening agent and is obtained by equation (3), is thus a spectrum having a steep peak in the wavelength range of 400 to 500 nm. Oppositely, when a light source, which contains a high amount of ultraviolet components, is used as the first light source and a light source, which hardly contains any ultraviolet components, is used as the second light source, the spectrum of the differential component $Fp(\lambda)$, which is due to the fluorescent whitening agent and is obtained by equation (3), will be a valley-shaped spectrum with negative values.

For practical purposes, it is convenient to perform the procedures of step S1 and step S2 on various types of paper, determine the spectra indicating the differential component $Fp(\lambda)$ due to the fluorescent whitening agent for each of the various types of paper, and store these spectra as data in advance. For example, by preparing information, which for example indicates the differential component spectra due to fluorescent whitening agent according to the type number of paper and paper manufacturing company, in the form of a database, the procedures of step S1 and step S2 can be omitted subsequently. Since obviously the contents of such a database will differ according to each light source combination, a database is preferably prepared for each of generally-used combinations of light sources. From such a standpoint, it can be said that the procedures of step S1 and step S2 are preparatory procedures.

FIG. 10 is a diagram, which illustrates the procedures of steps S3 and S4 in the flowchart shown in FIG. 2, and these procedures are procedures of the actual measurement stage in which measurements and calculations are performed for actual samples. First in step S3, the intensity of reflected light is measured for a sample (printed matter of dot percent S), which is the object of measurement, using a spectral radiance meter under illumination by the first light source T to determine the spectral reflectance $Rt(\lambda, S)$. In this process, the correction computation that makes use of a perfect reflecting diffuser plate is carried out as has been described above. Subsequently in step S4, computation based on equation (6) or equation (9) is performed to obtain the estimated spectral reflectance under illumination by the second light source U. In this computation, a correction term, obtained by multiplying the differential component Fp($\lambda$), which is due to the fluorescent whitening agent and has been determined in step S2, by a prescribed effective coefficient, is added to the spectral reflectance Rt($\lambda$, S) measured in step S3 under illumination by the first light source T.

In the process of step S40 of FIG. 2, the selection of which effective coefficient is to be used is made. In the case where the ink layer is regarded to be a perfectly hiding layer, since the effective coefficient will be $(1-S)^2$, the dot percent S is measured in step S41 and the estimated spectral reflectance Rtu($\lambda$, S) of the sample under illumination by the second light source U is determined by computation using equation (6). Meanwhile, in the case where it is regarded that light is transmitted through the ink layer and the effects of the fluorescence components occur, since the effective coefficient will be $(1-S(1-CE)) \cdot (1-S(1-CL))$, the excitation coefficient CE and emission coefficient CL of the sample are first determined in step S42 and thereafter, the dot percent S is measured in step S43 and the estimated spectral reflectance RRtu($\lambda$, S) of the sample under illumination by the second light source U is determined by computation using equation (9).

The results of application of this invention to a specific printed matter shall now be described. With this example, a tungsten lamp was used as the first light source T and CIE standard illuminant D65, stipulated in ISO/CIE 10526, was used as the second light source U. First, as shown in step S1 of FIG. 9, spectral reflectances were measured using a spectral radiance meter in conditions where a blank paper and a perfect reflecting diffuser were illuminated by the respective light sources to determine the inherent spectral reflectances Pt($\lambda$) and Pu($\lambda$) of the paper. Then as shown in step S2, the spectrum data, corresponding to the differential component Fp($\lambda$) due to the fluorescent whitening agent, were determined as the difference between the inherent spectral reflectances Pt($\lambda$) and Pu($\lambda$). Four types of sample, for which the dot percent was 0%, 20%, 60%, and 100%, were then prepared using black ink, and for each of these four types of sample, light from the first light source T, comprised of a tungsten lamp, was irradiated and measured values of the spectral reflectance Rt($\lambda$, S) were obtained using a spectral radiance meter, as shown in step S3 of FIG. 10. Then in step S4, the use of the effective coefficient, $(1-S(1-CE)) \cdot (1-S(1-CL))$, was selected, that is, it was considered that light is transmitted through the ink layer and the effects of the fluorescence components occur, and the estimated spectral reflectance RRtu($\lambda$, S) was determined for each sample by computation using equation (9).

Also, in order to verify that these estimated spectral reflectances RRtu($\lambda$, S) indicate correct evaluation standards of the colors of the samples when observed under illumination by the second light source U, the spectral reflectance Ru($\lambda$, S) of each of the four types of sample was measured using a spectral radiance meter under illumination by the CIE standard illuminant D65. This measurement procedure corresponds to using the CIE standard illuminant D65 (second light source U) in place of the tungsten lamp (first light source T) in the measurement procedure shown in step S3 of FIG. 10.

Figure 11:
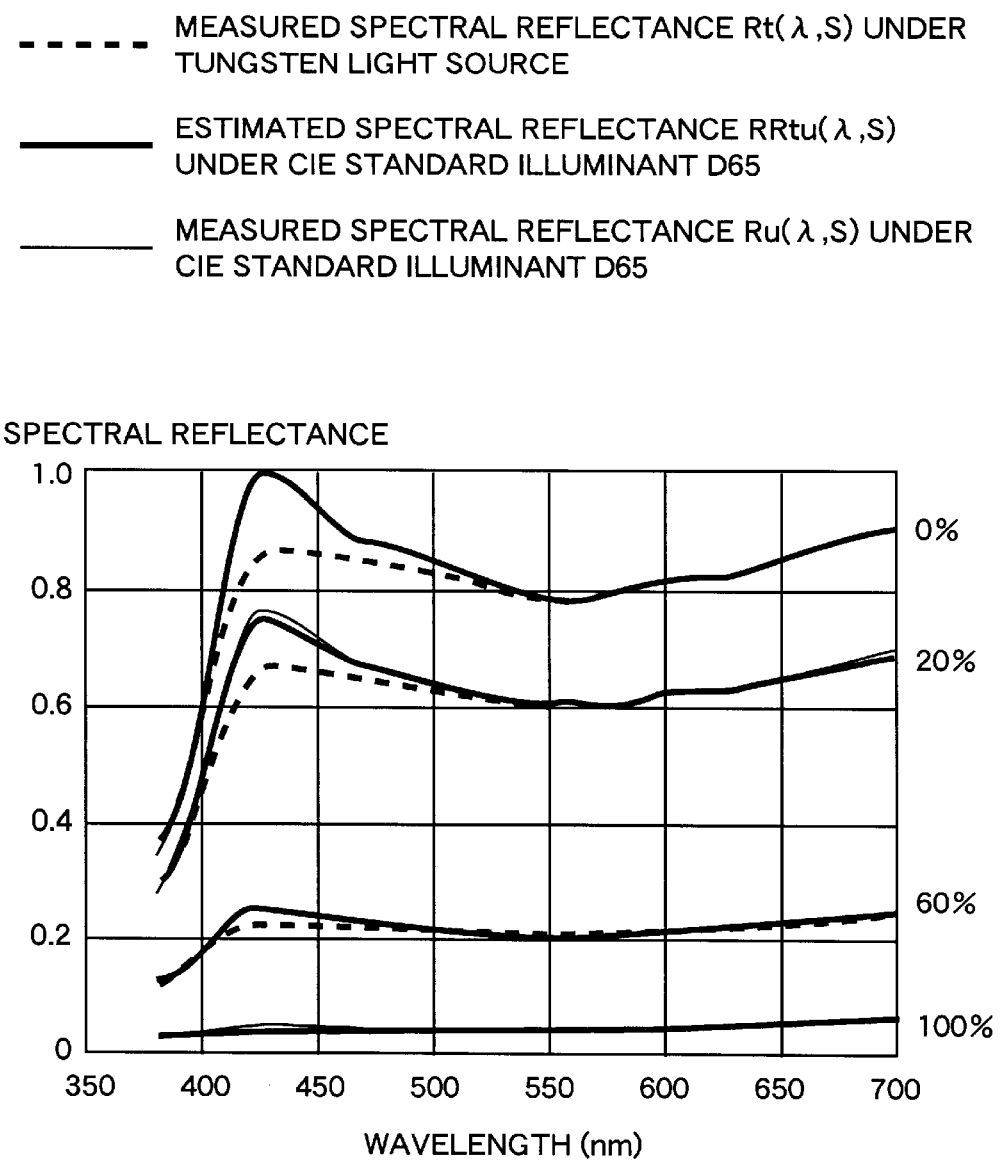
FIG. 11 shows graphs that compare three types of spectra obtained from four types of sample.

FIG. 11 shows graphs that compare three types of spectra obtained from the four types of sample. The numerical values of 0%, 20%, 60%, and 100%, which are shown at the right side of the graphs indicate that the respective graphs show the spectral reflectance concerning the respective samples with dot percents of 0%, 20%, 60%, and 100%. The broken line graphs indicate the spectral reflectances Rt($\lambda$, S) that were measured under the illumination environment of the first light source T (tungsten lamp) (step S3). The thick solid line graphs indicate the estimated spectral reflectances RRtu($\lambda$, S) under the illumination environment of the second light source U (CIE standard illuminant D65) that were obtained by performing the computation of step S4 on the graphs indicated by the broken lines. Furthermore, the thin solid line graphs (the graphs for dot percents of 0% and 60% cannot be recognized due to being overlapped with the corresponding graphs indicated by thick solid lines) indicate the spectral reflectances Ru($\lambda$, S) that were measured under the illumination environment of the second light source U (CIE standard illuminant D65) for verification of the effects of this invention.

These results show that large differences exist between the broken line graphs and the corresponding thin solid line graphs (which are overlapped with the thick solid line graphs in most parts) in the wavelength range in the vicinity of 400 to 500 nm (wavelength range of the fluorescence that is emitted by the fluorescent whitening agent). That is, comparison of the actually measured value show that, even for the same sample, the spectra of spectral reflectance will differ greatly when the light source is different. However, the thick solid line graphs and thin solid lines graph are matched at considerable precision, and it can thus be understood that the estimated spectral reflectance under the second light source U that has been calculated by this invention provides results that are considerably close to the measured spectral reflectance under the same second light source U.

As has been mentioned above, in a general color measuring device, a tungsten lamp is used in many cases in order to make the device itself compact. By using the present invention, even if the spectral reflectance of the sample is measured using such a tungsten lamp, the estimated spectral reflectance, for example under illumination by a fluorescent lamp, can be determined by performing a correction computation on the measured values. Correct color evaluation standards under an arbitrary illumination environment can thus be provided if measurements are made using a tungsten lamp.

<<< Section 3. Colorimetric Value Measurement Procedures by the Color Measuring Method of this Invention >>>

Up until now, the method of determining the spectral reflectance of a sample, comprised of printed matter, under an illumination environment that differs from that of actual measurement has been described. However, the spectral reflectance data are data on the reflectance spectrum in the visible wavelength range of 380 nm to 780 nm and are inconvenient to handle in practical work. Colorimetric values, defined by tristimulus values (XYZ) of the XYZ colorimetric system, stipulated by the Commission Internationale de l'Eclairage (CIE), are thus generally used in color evaluation. The basic principles of the color measuring method for printed matter of this invention is not only applicable to the determination of spectral reflectance but is also applicable to the determination of colorimetric values defined by XYZ tristimulus values (shall be referred to hereinafter simply as "colorimetric values"). Here, a modification example of applying the method concerning spectral reflectance, which has been described up until now, to colorimetric values shall be described.

The basic working procedures for determining colorimetric values are the same as the spectral reflectance determination procedures, which have been described up until now. However, the computing equations that are used differ somewhat. The differences in the computing equations shall now be described with reference to the diagrams of FIGS. 9 and 10.

First in step S1, a spectral radiance meter is used to measure reflected light intensities of the same paper under illumination by the first light source T and under illumination by the second light source U, respectively, and corrections using a perfect reflecting diffuser are carried out to determine the spectral reflectances $Pt(\lambda)$ and $Pu(\lambda)$ in the same manner as the above-described procedure. Colorimetric values (tristimulus values (XYZ) of the XYZ colorimetric system) of the paper under illumination by the first light source T are then determined from the spectral reflectance $Pt(\lambda)$ that has been obtained. Here, the colorimetric values shall be indicated as Pt(X), Pt(Y), and Pt(Z). Likewise, the colorimetric values Pu(X), Pu(Y), and Pu(Z) of the paper under illumination by the second light source U are determined from the spectral reflectance $Pu(\lambda)$. For the determination of the tristimulus values (XYZ) based on spectral reflectance, a known method that uses the spectral sensitivity distribution of the human visual system and the spectral intensity distribution of the light source used in observation (refer for example to ISO/CIE 10527 CIE standard colorimetric observers, 1st Ed., 1991) can be used, and thus a description thereof shall be omitted here.

Subsequently, the following equations (12) are used to calculate the colorimetric values Fp(X), Fp(Y), and Fp(Z), concerning the differential component due to the fluorescent whitening agent contained in the paper, as differences in the colorimetric values under the two different light sources.

$$Fp(X)=Pu(X)-Pt(X)$$

$$Fp(Y)=Pu(Y)-Pt(Y)$$

$$Fp(Z)=Pu(Z)-Pt(Z) \tag{12}$$

This corresponds to the procedure of determining the differential component $Fp(\lambda)$ due to the fluorescent whitening agent by using equation (3) in step S2 of the formerly described procedures. That is, the colorimetric values Fp(X), Fp(Y), and Fp(Z) determined by equations (12) correspond to the spectrum of $Fp(\lambda)$ indicated in step S2 of FIG. 9.

For practical use, the colorimetric values Fp(X), Fp(Y), and Fp(Z) maybe determined in advance for various types of paper and various combinations of light sources and accumulated in a database, and by using these values as necessary, the performing of step S1 and step S2 each time may be eliminated.

Subsequently, the procedures of the stage of actual measurement of an actual sample are carried out. First, as shown in step S3 of FIG. 10, the intensity of reflected light of a sample (printed matter of dot percent S), which is the object of measurement, is measured using a spectral radiance meter under illumination by the first light source T and correction using a perfect reflecting diffuser is performed to determine the spectral reflectance $Rt(\lambda, S)$. Then from the spectral reflectance $Rt(\lambda, S)$ that has been obtained, the colorimetric values Rt(X, S), Rt(Y, S), and Rt(Z, S) of the sample under the illumination environment of the first light source T are determined.

Lastly, computations corresponding to step S4 of FIG. 10 are performed to determine the estimated colorimetric values of the sample under the illumination environment of the second light source U. The estimated colorimetric values Ptu(X), Ptu(Y), and Ptu(Z) of the paper in the blank condition can be defined by equations (13).

$$Ptu(X)=Pt(X)+Fp(X)$$

$$Ptu(Y)=Pt(Y)+Fp(Y)$$

$$Ptu(Z)=Pt(Z)+Fp(Z) \tag{13}$$

These equations (13) correspond to equation (5). In the equations (13), the fluorescence components emitted from the fluorescent whitening agent are compensated by adding the differential components Fp(X), Fp(Y) and Fp(Z) which have been obtained by equations (12). The suffix tu in equations (13) indicates that an estimated value is an "estimated value under the second light source U" that has been determined by computation from the "measured value under the first light source T."

On the other hand, in the case of a sample that is comprised of printed matter, since the effects of the differential components due to the fluorescent whitening agent that have been obtained by equations (12) are not exhibited by 100%, additions must be performed upon multiplying the differential components by predetermined effective factors. In the case where the ink layer is regarded as being a perfectly hiding layer as indicated in step S4 of FIG. 10, the effective coefficient will be $(1-S)^2$, and in the case where it is regarded that light is transmitted through the ink layer and gives rise to the effects of the fluorescence components, the effective coefficient will be $(1-S(1-CE)) \cdot (1-S(1-CL))$. The estimated colorimetric values Rtu(X, S), Rtu(Y, S), and Rtu(Z, S) of the sample under the illumination environment of the second light source U, which are determined along the former line of thought, are obtained by equations (14).

$$Rtu(X, S)=Rt(X, S)+Fp(X) \cdot (1-S)^2$$

$$Rtu(Y, S)=Rt(Y, S)+Fp(X) \cdot (1-S)^2$$

$$Rtu(Z, S)=Rt(Z, S)+Fp(Z) \cdot (1-S)^2 \tag{14}$$

These equations (14) correspond to equation (6). Meanwhile, the estimated colorimetric values RRtu(X, S), RRtu(Y, S), and RRtu(Z, S) of the sample under the illumination environment of the second light source U, which are determined along the latter line of thought, are obtained by equation (15).

$$RRtu(X, S)=Rt(X, S)+Fp(X) \cdot (1-S(1-CE)) \cdot (1-S(1-CL))$$

$$RRtu(Y, S)=Rt(Y, S)+Fp(Y) \cdot (1-S(1-CE)) \cdot (1-S(1-CL))$$

$$RRtu(Z, S)=Rt(Z, S)+Fp(Z) \cdot (1-S(1-CE)) \cdot (1-S(1-CL)) \tag{15}$$

These equations (15) correspond to equation (9).

Though a description shall be omitted here, even for a sample in which halftone dots of a plurality of inks have been formed as shown in FIG. 8, estimated colorimetric values can be determined by carrying out computations corresponding to equation (11).

Lastly, the experimental results of applying the color measurement method for colorimetric values by this invention to an actual printed matter sample shall be described. First, a predetermined sample was prepared, the measured colorimetric values Rt(X, S), Rt(Y, S) and Rt(Z, S) were determined by measurement using a tungsten lamp, and by applying these values to equations (15), the estimated colorimetric values RRtu(X, S), RRtu(Y, S) and RRtu(Z, S) under illumination by CIE standard illuminant D65 were obtained. Furthermore, these colorimetric values were converted to Lab values. In order for verification of the accuracy, actual colorimetric values of the sample under illumination by CIE standard illuminant D65 are measured. Consequently, though an average color difference of 3.44 and a maximum color difference of 5.14 were seen in comparison of the measured values under illumination by the tungsten lamp and that under illumination by the CIE standard illuminant D65, the average color difference was reduced to 1.03 and the maximum color difference was reduced to 2.52 in comparison of the estimated values that were computed using equations (15) and the measured values under illumination by the CIE standard illuminant D65. The validity of this invention has thus been demonstrated by this experiment as well.

<<< Section 4. Color Measuring Device for Printed Matter by this Invention >>>

Figure 12:
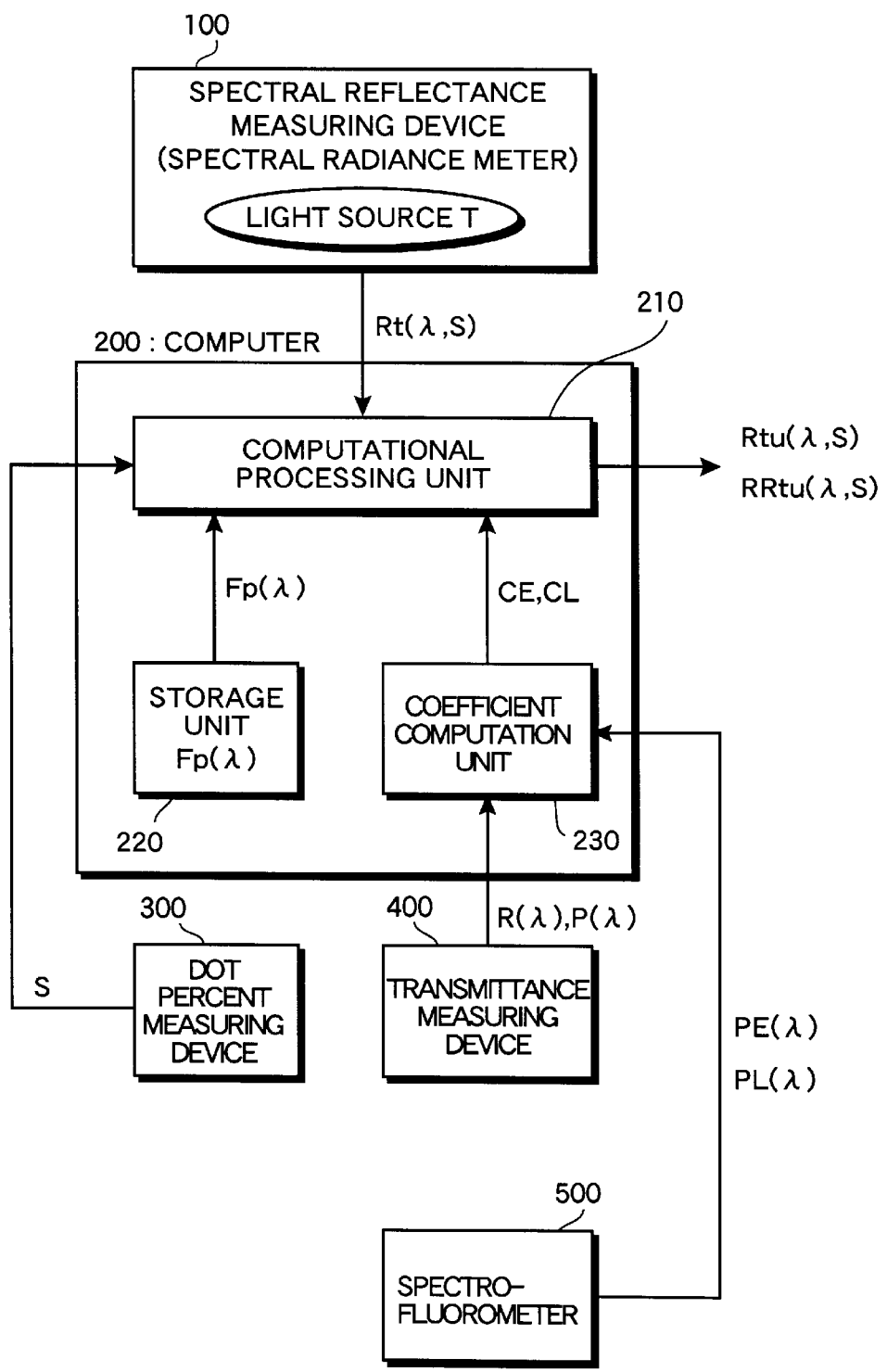
FIG. 12 is a block diagram, which illustrates the basic arrangement of a color measuring device for printed matter of an embodiment of this invention.

Finally, a color measuring device, which makes use of the color measuring method for printed matter that has been described up until now, shall be described. FIG. 12 is a block diagram, which illustrates the basic arrangement of a color measuring device for printed matter of an embodiment of this invention. This color measuring device determines the spectral reflectance under a predetermined illumination environment for a printed matter which is printed on a paper that contains a fluorescent whitening agent. The color measuring device basically includes, as illustrated, a spectral reflectance measuring device 100, a computer 200, a dot percent measuring device 300, transmittance measuring device 400, and spectrofluorometer 500. Here, in view of its functions, computer 200 can be regarded as being arranged of the three components of computational processing unit 210, storage unit 220, and coefficient computation unit 230.

Spectral reflectance measuring device 100 includes a first light source T and has a function of measuring the spectral reflectance of a measured object under the illumination environment of the first light source T. To be more specific, spectral reflectance measuring device 100 can be arranged from a general spectral radiance meter. A spectral radiance meter that incorporates, for the purpose of making the device compact and for practical reasons, a tungsten lamp as light source T is widely used. Thus with this invention, it is sufficient to use a general spectral radiance meter, in which a tungsten lamp is incorporated as light source T, as spectral reflectance measuring device 100. This spectral reflectance measuring device 100 is also equipped with a function of performing measurement using a perfect reflecting diffuser to obtain a spectral reflectance that is not influenced by the spectral intensity distribution of the first light source T.

Storage unit 220 stores a spectral data of differential component $Fp(\lambda)$ which is obtained by subtracting the spectral reflectance $Pt(\lambda)$ of a specific paper under the illumination environment of the first light source T from the spectral reflectance $Pu(\lambda)$ of the same paper under the illumination environment of the second light source U. This differential component $Fp(\lambda)$ will differ according to the combination of the light source and will also differ according to the type of paper. Thus for practical purposes, it is preferable to store the spectral data of differential component $Fp(\lambda)$ in the form of a database in storage unit 220 and enable the spectral data of differential component $Fp(\lambda)$ for a specific type of paper and specific combination of light sources to be read and used as necessary. Obviously, if the second light source U can be made available, the spectral reflectance $Pt(\lambda)$ and the spectral reflectance $Pu(\lambda)$ of a specific type of paper can be measured using spectral reflectance measuring device 100 and the differential component $Fp(\lambda)$ can be determined at the same time and used upon storage in storage unit 220. The differential component $Fp(\lambda)$ that is stored in the storage unit 220 corresponds to the differential component $Fp(\lambda)$ due to fluorescent whitening agent, which is indicated in step S4 of FIG. 10.

Coefficient computation unit 230 performs the computations for determining the excitation coefficient CE and luminescence coefficient CL of an ink-adhered part. As has been mentioned in Section 1, the excitation coefficient CE and luminescence coefficient CL are determined by the computations indicated by equations (7) and (8). Coefficient computation unit 230 has the function of performing such computations. As indicated by equations (7) and (8), the data of the spectral transmittance $R(\lambda)$ of the ink-adhered part in the measured region, the spectral transmittance $P(\lambda)$ of the non-ink-adhered part in the measured region, the excitation spectrum $PE(\lambda)$ of the paper, and the luminescence spectrum $PL(\lambda)$ of the paper are necessary for determining the excitation coefficient CE and luminescence coefficient CL. Transmittance measuring device 400 and spectrofluorometer 500 are devices for preparing these data.

That is, transmittance measuring device 400 has the function of measuring the spectral transmittance $R(\lambda)$ of the ink-adhered part and the spectral transmittance $P(\lambda)$ of the non-ink-adhered part based on the principles explained on FIGS. 4 through 7. As has been mentioned already and as shown in FIG. 4, for practical purposes, the spectral transmittances $R(\lambda)$ and $P(\lambda)$ can be measured by measuring the output light OutR' and OutP' that are emitted upwards instead of measuring the output light OutR and OutP that are emitted downwards. Transmittance measuring device 400 may thus be arranged using a general spectral radiance meter (the spectral radiance meter used in spectral reflectance measuring device 100 may be used).

Meanwhile, spectrofluorometer 500 is a device that is widely used for measuring the excitation spectrum and luminescence spectrum of arbitrary objects containing fluorescent components, and by carrying out a measurement with paper as the object, the excitation spectrum $PE(\lambda)$ and luminescence spectrum $PL(\lambda)$ of the paper are obtained. By measuring the excitation spectrum $PE(\lambda)$ and luminescence spectrum $PL(\lambda)$ of various types of paper in advance and storing the results as data in coefficient computation unit 230, the spectrofluorometer 500 can be removed from the arrangement of this color measuring device.

Dot percent measuring device 300 measures the area ratio S of an ink-adhered region with respect to the entire area within the measured region. In the case where the printed matter to be measured is printed by offset printing, the ink-adhered region within the measured region will be constituted by several halftone dots. A dot percent meter is widely used as a device for measuring the area ratios for such halftone dots and this may be used as dot percent measuring device 300. The area ratio S (dot percent) that has been measured by dot percent measuring device 300 is given to processing unit 210. In the case where the dot percent in the measured region can be recognized from the DTP data on which the printed matter is based, the recognized dot percent may be input directly into processing unit 210. In the case where such a form of use is to be employed, dot percent measuring device 300 can be removed from the arrangement of this color measuring device.

Computational processing unit 210 carries out a correction, based on the differential component $Fp(\lambda)$ stored in storage unit 220, on the spectral reflectance $Rt(\lambda, S)$ of the measured region of the specific printed matter that has been measured by spectral reflectance measuring device 100 to compute the estimated spectral reflectance of the measured region under the illumination environment of the second light source U. As has been mentioned above, the computation is performed based on equation (6) or equation (9). Equation (6) is an equation that can be applied in the case of performing processes that handle the ink layer as a perfectly hiding layer and enables the determination of the estimated spectral reflectance $Rtu(\lambda, S)$. Since the excitation coefficient CE and luminescence coefficient CL are unnecessary for performing the computation based on equation (6), in the case where a color measuring device that executes only the computation based on equation (6) is to be arranged, there is no need to provide coefficient computation unit 230, transmittance measuring device 400, and spectrofluorometer 500. Meanwhile, equation (9) is an equation that can be applied in the case where the light that is transmitted through the ink layer is taken into consideration by use of excitation coefficient CE and luminescence coefficient CL and enables the determination of estimated spectral reflectance RRtu($\lambda$, S).

Though the color measuring device for printed matter shown in FIG. 12 is a device that determines estimated spectral reflectances, this invention can also be applied, as has been explained in Section 3, in the case where color is expressed by XYZ tristimulus values. The device shown in FIG. 12 may thus also be used as a device for determining estimated XYZ tristimulus values. In this case, computational processing means 210 outputs XYZ tristimulus values in place of estimated spectral reflectances.

Also, since the computational processing unit 210, storage unit 220, and coefficient computation unit 230 of the color measuring device shown in FIG. 12 are components that are actually arranged by computer 200, all of these can be realized by incorporating programs for executing the above-described processes in a computer. Such programs may also be recorded in a recording medium that can be read by a computer and distributed.

By using the color measuring device for printed matter by this invention, which has been described above, correct color evaluation standards can be indicated even when a printed matter is observed under a light source that differs from the light source used for color measurement.

What is claimed is:

1. A color measuring method for determining a spectral reflectance, under a predetermined illumination environment, for printed matter including a paper containing a fluorescent whitening agent, the method being comprised of:

a first step of measuring a spectral reflectance Pt($\lambda$) of said paper under a first illumination environment and a spectral reflectance Pu($\lambda$) of said paper under a second illumination environment;

a second step of computing a difference, obtained by subtracting said spectral reflectance Pt($\lambda$) from said spectral reflectance Pu($\lambda$), as a differential component Fp($\lambda$) of said paper due to the fluorescent whitening agent;

a third step of measuring a spectral reflectance Rt($\lambda$), under said first illumination environment, for a region to be measured of said printed matter; and a fourth step of performing a correction based on said differential component Fp($\lambda$) on said spectral reflectance Rt($\lambda$) to compute an estimated spectral reflectance, under said second illumination environment, for said region to be measured, wherein:

in a process of computation in the fourth step, correction based on the differential component Fp($\lambda$) is not performed on an ink-adhered region within the region to be measured.

2. A color measuring method for printed matter as set forth in claim 1, wherein:

in a process of measurement in the first step and the third step, a result of measurement of a spectral reflectance of a perfect reflecting diffuser is used to perform a correction of eliminating influence of spectral intensity distribution of illumination light that is used.

3. A color measuring method for printed matter as set forth in claim 1, wherein:

in the third step, a spectral reflectance Rt($\lambda$, S) under the first illumination environment is measured for a region to be measured, a ratio of an area of an ink-adhered region to an entire area in said region to be measured being S;

in the fourth step, a computation using an equation:

$$Rtu(\lambda, S) = Rt(\lambda, S) + Fp(\lambda) \cdot (1-S)^2$$

is performed to determine an estimated spectral reflectance Rtu($\lambda$, S), under the second illumination environment, for said region to be measured.

4. A color measuring method for printed matter determining a spectral reflectance, under a predetermined illumination environment, for printed matter including a paper containing a fluorescent whitening agent, the method being comprised of:

a first step of measuring a spectral reflectance Pt($\lambda$) of said paper under a first illumination environment and a spectral reflectance Pu($\lambda$) of said paper under a second illumination environment;

a second step of computing a difference, obtained by subtracting said spectral reflectance Pt($\lambda$) from said spectral reflectance Pu($\lambda$), as a differential component Fp($\lambda$) of said paper due to the fluorescent whitening agent;

a third step of measuring a spectral reflectance Rt($\lambda$), under said first illumination environment, for a region to be measured of said printed matter; and a fourth step of performing a correction based on said differential component Fp($\lambda$) on said spectral reflectance Rt($\lambda$) to compute an estimated spectral reflectance, under said second illumination environment, for said region to be measured, wherein:

in a process of computation in the fourth step, a correction based on the differential component Fp($\lambda$) is performed in accordance to an optical transmittance of an ink layer for an ink-adhered region in the region to be measured.

5. A color measuring method for printed matter as set forth in claim 4, wherein:

in the third step, a spectral reflectance Rt($\lambda$, S) under the first illumination environment is measured for a region to be measured, a ratio of an area of an ink-adhered region to an entire area in said region to be measured being S;

in the fourth step, an excitation coefficient CE and a luminescence coefficient CL are defined, said excitation coefficient CE indicating a proportion of "total amount of excitation energy supplied to an ink-adhered part" per unit area with respect to "total amount of excitation energy supplied to a non-ink-adhered part" per unit area in the case where said parts are illuminated under the same conditions from an exterior, said luminescence coefficient CL indicating a proportion of "total amount of luminescence energy emitted from the ink-adhered part and observed" per unit area with respect to "total amount of luminescence energy emitted from the non-ink-adhered part and observed" per unit area in the case where emission of fluorescence from each of said parts occurs under the same conditions inside the paper, the excitation coefficient CE and the luminescence coefficient CL of said region to be measured are measured, and computation using an equation:

$$RRtu(\lambda, S)=Rt(\lambda, S)+Fp(\lambda)\cdot(1-S(1-CE))\cdot(1-S(1-CL))$$

is performed to determine an estimated spectral reflectance RRtu($\lambda$, S), under the second illumination environment, for said region to be measured.

6. A color measuring method for printed matter as set forth in claim 5, wherein:

a spectral transmittance R($\lambda$) of the ink-adhered part, a spectral transmittance P($\lambda$) of the non-ink-adhered part, an excitation spectrum PE($\lambda$) of the paper, and a luminescence spectrum PL($\lambda$) of the paper are measured; and the excitation coefficient CE and the luminescence coefficient CL of said ink-adhered part are determined using the following equations:

$$CE=\int R(\lambda)\cdot PE(\lambda)d\lambda / \int P(\lambda)\cdot PE(\lambda)d\lambda$$

$$CL=\int R(\lambda)\cdot PL(\lambda)d\lambda / \int P(\lambda)\cdot PL(\lambda)d\lambda.$$

7. A color measuring method for printed matter as set forth in claim 4, wherein:

in the third step, a spectral reflectance $Rt(\lambda, S_1, S_2, S_{12})$ under the first illumination environment is measured for a region to be measured, ratios of areas of a first region, a second region, a third region and a fourth region with respect to an entire area in said region to be measured being $S_1, S_2, S_{12}, S_p$, respectively, only a first ink being adhered in said first region, only a second ink being adhered in said second region, both the first ink and the second ink being adhered in said third region, and neither ink being adhered in said fourth region;

in the fourth step, an excitation coefficient CE and a luminescence coefficient CL are defined, said excitation coefficient CE indicating a proportion of "total amount of excitation energy supplied to an ink-adhered part" per unit area with respect to "total amount of excitation energy supplied to a non-ink-adhered part" per unit area in the case where said parts are illuminated under the same conditions from an exterior, said luminescence coefficient CL indicating a proportion of "total amount of luminescence energy emitted from the ink-adhered part and observed" per unit area with respect to "total amount of luminescence energy emitted from the non-ink-adhered part and observed" per unit area in the case where emission of fluorescence from each of said parts occurs under the same conditions inside the paper, excitation coefficients $CE_1$, $CE_2$, and $CE_{12}$ and luminescence coefficients $CL_1$, $CL_2$, and $CL_{12}$ of said first region, said second region, and said third region, respectively, are measured, and computation using an equation:

$$RRtu(\lambda, S_1, S_2, S_{12})=Rt(\lambda, S_1, S_2, S_{12})+Fp(\lambda)\cdot(S_p+S_1\cdot CE_1+S_2\cdot CE_2+S_{12}\cdot CE_{12})\cdot(S_p+S_1\cdot CL_1+S_2\cdot CL_2+S_{12}\cdot CL_{12})$$

is performed to determine an estimated spectral reflectance RRtu($\lambda$, $S_1$, $S_2$, $S_{12}$), under the second illumination environment, for said region to be measured.

8. A color measuring method for printed matter as set forth in claim 7, wherein:

a spectral transmittance R($\lambda$) of the ink-adhered part, a spectral transmittance P($\lambda$) of the non-ink-adhered part, an excitation spectrum PE($\lambda$) of the paper, and a luminescence spectrum PL($\lambda$) of the paper are measured; and the excitation coefficient CE and the luminescence coefficient CL of said ink-adhered part are determined using the following equations:

$$CE=\int R(\lambda)\cdot PE(\lambda)d\lambda / \int P(\lambda)\cdot PE(\lambda)d\lambda$$

$$CL=\int R(\lambda)\cdot PL(\lambda)d\lambda / \int P(\lambda)\cdot PL(\lambda)d\lambda.$$

9. A color measuring method for printed matter as set forth in claim 6, wherein:

in the third step, a spectral reflectance under the first illumination environment is measured for a region to be measured, on which printing using a plurality of inks is performed and a total of n kinds of ink-adhered regions are formed by mixing of a first type of region in which only an ink of a single color is adhered and a second type of region in which a plurality of inks are adhered in an overlapping manner, a ratio of an area of an i-th region with respect to an entire area in said region to be measured being Si;

in the fourth step, an excitation coefficient CE and a luminescence coefficient CL are defined, said excitation coefficient CE indicating a proportion of "total amount of excitation energy supplied to an ink-adhered part" per unit area with respect to "total amount of excitation energy supplied to a non-ink-adhered part" per unit area in the case where said parts are illuminated under the same conditions from an exterior, said luminescence coefficient CL indicating a proportion of "total amount of luminescence energy emitted from the ink-adhered part and observed" per unit area with respect to "total amount of luminescence energy emitted from the non-ink-adhered part and observed" per unit area in the case where emission of fluorescence from each of said parts occurs under the same conditions inside the paper, and the excitation coefficient CE and the luminescence coefficient CL of each of said n kinds of ink-adhered regions are measured; and in a process of computation in the fourth step, a correction based on the differential component Fp($\lambda$) is performed on said n kinds of ink-adhered regions in said region to be measured in accordance to the excitation coefficients CE and the luminescence coefficients CL determined for the respective n kinds of ink-adhered regions.

10. A color measuring method for printed matter as set forth in claim 9, wherein:

a spectral transmittance R($\lambda$) of the ink-adhered part, a spectral transmittance P($\lambda$) of the non-ink-adhered part, an excitation spectrum PE($\lambda$) of the paper, and a luminescence spectrum PL($\lambda$) of the paper are measured; and the excitation coefficient CE and the luminescence coefficient CL of said ink-adhered part are determined using the following equations:

$$CE=\int R(\lambda)\cdot PE(\lambda)d\lambda / \int P(\lambda)\cdot PE(\lambda)d\lambda$$

$$CL=\int R(\lambda)\cdot PL(\lambda)d\lambda / \int P(\lambda)\cdot PL(\lambda)d\lambda.$$

11. A color measuring method for printed matter as set forth in claim 4, wherein:

in a process of measurement in the first step and the third step, a result of measurement of a spectral reflectance of a perfect reflecting diffuser is used to perform a correction of eliminating influence of spectral intensity distribution of illumination light that is used.

12. A color measuring method for determining XYZ tristimulus values, under a predetermined illumination environment, for a printed matter including a paper containing a fluorescent whitening agent, the method being comprised of:

a first step of measuring XYZ tristimulus values Pt(X), Pt(Y), and Pt(Z) of said paper under a first illumination environment and XYZ tristimulus values Pu(X), Pu(Y), and Pu(Z) of said paper under a second illumination environment;

a second step of computing differences, obtained by subtracting said XYZ tristimulus values Pt(X), Pt(Y), and Pt(Z) from said XYZ tristimulus values Pu(X), Pu(Y), and Pu(Z), respectively, as differential components Fp(X), Fp(Y), and Fp(Z) of said paper due to the fluorescent whitening agent;

a third step of measuring XYZ tristimulus values Rt(X), Rt(Y), and Rt(Z), under said first illumination environment, for a region to be measured of said printed matter; and a fourth step of performing corrections based on said differential components Fp(X), Fp(Y), and Fp(Z) on said XYZ tristimulus values Rt(X), Rt(Y), and Rt(Z), respectively, to compute estimated XYZ tristimulus values, under said second illumination environment, for said region to be measured.

13. A color measuring method for printed matter as set forth in claim 12, wherein:

in a process of measurement in the first step and the third step, XYZ tristimulus values are determined by computation using spectral reflectances obtained by measurement.

14. A color measuring method for printed matter as set forth in claim 12, wherein:

in a process of computation in the fourth step, corrections based on the differential components Fp(X), Fp(Y), and Fp(Z) are not performed on an ink-adhered region within the region to be measured.

15. A color measuring method for printed matter as set forth in claim 14, wherein:

in the third step, XYZ tristimulus values Rt(X, S), Rt(Y, S), and Rt(Z, S) under the first illumination environment is measured for a region to be measured, a ratio of an area of an ink-adhered region to an entire area in said region to be measured being S;

in the fourth step, computations using the following equations:

$$Rtu(X, S)=Rt(X, S)+Fp(X)\cdot(1-S)^2$$

$$Rtu(Y, S)=Rt(Y, S)+Fp(Y)\cdot(1-S)^2$$

$$Rtu(Z, S)=Rt(Z, S)+Fp(Z)\cdot(1-S)^2$$

are performed to determine estimated XYZ tristimulus values Rtu(X, S), Rtu(Y, S), and Rtu(Z, S), under the second illumination environment, for said region to be measured.

16. A color measuring method for printed matter as set forth in claim 12, wherein:

in a process of computation in the fourth step, corrections based on the differential components Fp(X), Fp(Y), and Fp(Z) are performed in accordance to an optical transmittance of an ink layer for an ink-adhered region in the region to be measured.

17. A color measuring method for printed matter as set forth in claim 16, wherein:

in the third step, XYZ tristimulus values Rt(X, S), Rt(Y, S), and Rt(Z, S) under the first illumination environment is measured for a region to be measured, a ratio of an area of an ink-adhered region to an entire area in said region to be measured being S;

in the fourth step, an excitation coefficient CE and a luminescence coefficient CL are defined, said excitation coefficient CE indicating a proportion of "total amount of excitation energy supplied to an ink-adhered part" per unit area with respect to "total amount of excitation energy supplied to a non-ink-adhered part" per unit area in the case where said parts are illuminated under the same conditions from an exterior, said luminescence coefficient CL indicating a proportion of "total amount of luminescence energy emitted from the ink-adhered part and observed" per unit area with respect to "total amount of luminescence energy emitted from the non-ink-adhered part and observed" per unit area in the case where emission of fluorescence from each of said parts occurs under the same conditions inside the paper, the excitation coefficient CE and the luminescence coefficient CL of said region to be measured are measured, and computations using the following equations:

$$RRtu(X, S)=Rt(X, S)+Fp(X)\cdot(1-S(1-CE))\cdot(1-S(1-CL))$$

$$RRtu(Y, S)=Rt(Y, S)+Fp(Y)\cdot(1-S(1-CE))\cdot(1-S(1-CL))$$

$$RRtu(Z, S)=Rt(Z, S)+Fp(Z)\cdot(1-S(1-CE))\cdot(1-S(1-CL))$$

are performed to determine estimated XYZ tristimulus values RRtu(X, S), RRtu(Y, S), and RRtu(Z, S), under the second illumination environment, for said region to be measured.

18. A color measuring method for printed matter as set forth in claim 17, wherein:

a spectral transmittance R(λ) of the ink-adhered part, a spectral transmittance P(λ) of the non-ink-adhered part, an excitation spectrum PE(λ) of the paper, and a luminescence spectrum PL(λ) of the paper are measured; and the excitation coefficient CE and the luminescence coefficient CL of said ink-adhered part are determined using the following equations:

$$CE=\int R(\lambda)\cdot PE(\lambda)d\lambda/\int P(\lambda)\cdot PE(\lambda)d\lambda$$

$$CL=\int R(\lambda)\cdot PL(\lambda)d\lambda/\int P(\lambda)\cdot PL(\lambda)d\lambda.$$

19. A color measuring method for printed matter as set forth in claim 16, wherein:

in the third step, XYZ tristimulus values under the first illumination environment are measured for a region to be measured, on which printing using a plurality of inks is performed and a total of n kinds of ink-adhered regions are formed by mixing of a first region in which only an ink of a single color is adhered and a second region in which a plurality of inks are adhered in an overlapping manner, a ratio of an area of an i-th region with respect to an entire area in said region to be measured being Si;

in the fourth step, an excitation coefficient CE and a luminescence coefficient CL are defined, said excitation coefficient CE indicating a proportion of "total amount of excitation energy supplied to an ink-adhered part" per unit area with respect to "total amount of excitation energy supplied to a non-ink-adhered part" per unit area in the case where said parts are illuminated under the same conditions from an exterior, said luminescence coefficient CL indicating a proportion of "total amount of luminescence energy emitted from the ink-adhered part and observed" per unit area with respect to "total amount of luminescence energy emitted from the non-ink-adhered part and observed" per unit area in the case where emission of fluorescence from each of said parts occurs under the same conditions inside the paper, and the excitation coefficient CE and the luminescence coefficient CL of each of said n kinds of ink-adhered regions are measured; and in a process of computation in the fourth step, corrections based on the differential components Fp(X), Fp(Y), and Fp(Z) are performed on said n kinds of ink-adhered regions in said region to be measured in accordance to the excitation coefficients CE and the luminescence coefficients CL determined for the respective n kinds of ink-adhered regions.

20. A color measuring method for printed matter as set forth in claim 19, wherein:

a spectral transmittance $R(\lambda)$ of the ink-adhered part, a spectral transmittance $P(\lambda)$ of the non-ink-adhered part, an excitation spectrum $PE(\lambda)$ of the paper, and a luminescence spectrum $PL(\lambda)$ of the paper are measured; and the excitation coefficient CE and the luminescence coefficient CL of said ink-adhered part are determined using the following equations:

$$CE = \int R(\lambda) \cdot PE(\lambda) d\lambda / \int P(\lambda) \cdot PE(\lambda) d\lambda$$

$$CL = \int R(\lambda) \cdot PL(\lambda) d\lambda / \int P(\lambda) \cdot PL(\lambda) d\lambda.$$

21. A color measuring device for determining a spectral reflectance, under a predetermined illumination environment, of printed matter including a paper containing a fluorescent whitening agent, the color measuring device being comprised of:

a spectral reflectance measuring device, which measures a spectral reflectance of an object to be measured under a first illumination environment;

a storage unit, which stores a differential component $Fp(\lambda)$, obtained by subtracting a spectral reflectance $Pt(\lambda)$ of a specific paper under said first illumination environment from a spectral reflectance $Pu(\lambda)$ of said paper under a second illumination environment; and a computational processing unit, which performs a correction based on said differential component $Fp(\lambda)$ on a spectral reflectance $Rt(\lambda)$, which is measured by said spectral reflectance measuring device for a region to be measured in the printed matter including said specific paper, to compute an estimated spectral reflectance, under said second illumination environment, for said region to be measured, wherein:

the computational processing unit has a function of inputting an area ratio S of an ink-adhered region with respect to an entire area within the region to be measured and performs computation using the following equation on a spectral reflectance $Rt(\lambda, S)$, which has been measured for said region to be measured by the spectral reflectance measuring device;

$$Rtu(\lambda, S) = Rt(\lambda, S) + Fp(\lambda) \cdot (1-S)^2$$

so as to determine an estimated spectral reflectance $Rtu(\lambda, S)$, under the second illumination environment, of said region to be measured.

22. A color measuring device for printed matter as set forth in claim 21, wherein:

a dot percent measuring device, which measures an area ratio S of an ink-adhered region with respect to an entire area within the region to be measured, is furthermore equipped.

23. A program, which makes a computer function as the computational processing unit in a color measuring device for printed matter as set forth in claim 21, or a computer-readable medium that stores said program.

24. A color measuring device for determining a spectral reflectance, under a predetermined illumination environment, of printed matter including a paper containing a fluorescent whitening agent, the color measuring device being comprised of:

a spectral reflectance measuring device, which measures a spectral reflectance of an object to be measured under a first illumination environment;

a storage unit, which stores a differential component $Fp(\lambda)$, obtained by subtracting a spectral reflectance $Pt(\lambda)$ of a specific paper under said first illumination environment from a spectral reflectance $Pu(\lambda)$ of said paper under a second illumination environment; and a computational processing unit, which performs a correction based on said differential component $Fp(\lambda)$ on a spectral reflectance $Rt(\lambda)$, which is measured by said spectral reflectance measuring device for a region to be measured in the printed matter including said specific paper, to compute an estimated spectral reflectance, under said second illumination environment, for said region to be measured, wherein:

the computational processing unit has a function of inputting, with regard to the region to be measured, an area ratio S of an ink-adhered region with respect to an entire area, an excitation coefficient CE, which indicates a proportion of "total amount of excitation energy supplied to the ink-adhered part" per unit area with respect to "total amount of excitation energy supplied to a non-ink-adhered part" per unit area in the case where said parts are illuminated under the same conditions from an exterior, and a luminescence coefficient CL, which indicates a proportion of "total amount of luminescence energy emitted from the ink-adhered part and observed" per unit area with respect to "total amount of luminescence energy emitted from the non-ink-adhered part and observed" per unit area in the case where emission of fluorescence from each of said parts occurs under the same conditions inside the paper, and performs computation using the following equation on a spectral reflectance $Rt(\lambda, S)$, which has been measured for said region to be measured by said spectral reflectance measuring device;

$$RRtu(\lambda, S) = Rt(\lambda, S) + Fp(\lambda) \cdot (1-S(1-CE)) \cdot (1-S(1-CL))$$

so as to determine an estimated spectral reflectance $RRtu(\lambda, S)$, under the second illumination environment, of said region to be measured.

25. A color measuring device for printed matter as set forth in claim 24, furthermore equipped with:

a dot percent measuring device, which measures an area ratio S of an ink-adhered region with respect to an entire area within the region to be measured;

a transmittance measuring device, which measures a spectral transmittance $R(\lambda)$ of an ink-adhered part in the region to be measured and a spectral transmittance P($\lambda$) of a non-ink-adhered part in the region to be measured; and a coefficient computation unit, which computes an excitation coefficient CE and a luminescence coefficient CL of said ink-adhered part, using said spectral transmittance R($\lambda$) and said spectral transmittance P($\lambda$) which have been measured by said transmittance measuring device, and an excitation spectrum PE($\lambda$) of the paper and a luminescence spectrum PL($\lambda$) of the paper in accordance to the following equations:

$$CE = \int R(\lambda) \cdot PE(\lambda) d\lambda / \int P(\lambda) \cdot PE(\lambda) d\lambda$$

$$CL = \int R(\lambda) \cdot PL(\lambda) d\lambda / \int P(\lambda) \cdot PL(\lambda) d\lambda.$$

26. A color measuring device for printed matter as set forth in claim 25, wherein:

a spectrofluorometer, which measures an excitation spectrum PE($\lambda$) of the paper and a luminescence spectrum PL($\lambda$) of the paper, is furthermore equipped and the coefficient computation unit uses the excitation spectrum PE($\lambda$) of the paper and the luminescence spectrum PL($\lambda$) of the paper measured by said spectrofluorometer in performing computation for determining the excitation coefficient CE and the luminescence coefficient CL.

27. A program, which makes a computer function as the computational processing unit in a color measuring device for printed matter as set forth in claim 24, or a computer-readable medium that stores said program.

28. A color measuring device for determining a spectral reflectance, under a predetermined illumination environment, of printed matter including a paper containing a fluorescent whitening agent, the color measuring device being comprised of:

a spectral reflectance measuring device, which measures a spectral reflectance of an object to be measured under a first illumination environment;

a storage unit, which stores a differential component Fp($\lambda$), obtained by subtracting a spectral reflectance Pt($\lambda$) of a specific paper under said first illumination environment from a spectral reflectance Pu($\lambda$) of said paper under a second illumination environment; and a computational processing unit, which performs a correction based on said differential component Fp($\lambda$) on a spectral reflectance Rt($\lambda$), which is measured by said spectral reflectance measuring device for a region to be measured in the printed matter including said specific paper, to compute an estimated spectral reflectance, under said second illumination environment, for said region to be measured, wherein:

the computational processing unit has a function of computing XYZ tristimulus values based on a predetermined spectral reflectance and computes estimated XYZ tristimulus values, under the second illumination environment, for the region to be measured.

29. A color measuring device for printed matter as set forth in claim 28, wherein:

the storage unit stores the differential component Fp($\lambda$) in a form of XYZ tristimulus values; and the computational processing unit performs computation using said differential component stored in the form of XYZ tristimulus values.

30. A program, which makes a computer function as the computational processing unit in a color measuring device for printed matter as set forth in claim 28, or a computer-readable medium that stores said program.

* * * * *

UNITED STATES PATENT AND TRADEMARK OFFICE
CERTIFICATE OF CORRECTION

PATENT NO.    : 6,671,050 B2
DATED         : December 30, 2003
INVENTOR(S)   : Tohru Sugiyama et al.

It is certified that error appears in the above-identified patent and that said Letters Patent is hereby corrected as shown below:

<u>Title page,</u>
Item [*] Notice, "30" should read -- 98 --.

Signed and Sealed this

Twenty-fourth Day of February, 2004

JON W. DUDAS
*Acting Director of the United States Patent and Trademark Office*